(12) United States Patent
Oishi et al.

(10) Patent No.: US 9,017,536 B2
(45) Date of Patent: *Apr. 28, 2015

(54) HEMOGLOBIN MEASUREMENT METHOD AND ELECTROPHORESIS APPARATUS

(75) Inventors: Kazuyuki Oishi, Osaka (JP); Izumi Omoto, Osaka (JP); Eriko Kusaka, Osaka (JP); Toshiki Kawabe, Osaka (JP)

(73) Assignee: Sekisui Chemical Co., Ltd., Osaka (JP)

(*) Notice: Subject to any disclaimer, the term of this patent is extended or adjusted under 35 U.S.C. 154(b) by 744 days.
This patent is subject to a terminal disclaimer.

(21) Appl. No.: 12/448,279

(22) PCT Filed: Dec. 26, 2007

(86) PCT No.: PCT/JP2007/074982
§ 371 (c)(1),
(2), (4) Date: Jul. 15, 2009

(87) PCT Pub. No.: WO2008/078781
PCT Pub. Date: Jul. 3, 2008

(65) Prior Publication Data
US 2010/0006436 A1    Jan. 14, 2010

(30) Foreign Application Priority Data

| Dec. 26, 2006 | (JP) | 2006-350209 |
|---|---|---|
| Dec. 27, 2006 | (JP) | 2006-353030 |
| Dec. 28, 2006 | (JP) | 2006-355979 |
| Jan. 12, 2007 | (JP) | 2007-005093 |
| Jan. 12, 2007 | (JP) | 2007-005094 |
| Jan. 19, 2007 | (JP) | 2007-010671 |
| Apr. 3, 2007 | (JP) | 2007-097626 |
| Apr. 16, 2007 | (JP) | 2007-107110 |
| Oct. 26, 2007 | (JP) | 2007-279186 |
| Oct. 26, 2007 | (JP) | 2007-279187 |
| Dec. 14, 2007 | (JP) | 2007-323910 |
| Dec. 19, 2007 | (JP) | 2007-326978 |

(51) Int. Cl.
*B01D 57/02* (2006.01)
*G01N 27/447* (2006.01)
*C07K 1/26* (2006.01)

(52) U.S. Cl.
CPC .......... *G01N 27/44747* (2013.01); *C07K 1/26* (2013.01); *G01N 2333/805* (2013.01)

(58) Field of Classification Search
USPC ............... 204/450–470, 546–550, 600–621, 204/641–645
See application file for complete search history.

(56) References Cited

U.S. PATENT DOCUMENTS

| 5,611,903 A * | 3/1997 | Janssens et al. ............... 204/454 |
| 2002/0028308 A1* | 3/2002 | Harada et al. ................. 428/34.4 |

(Continued)

FOREIGN PATENT DOCUMENTS

| EP | 0 733 900 | 9/1996 |
| EP | 1 022 562 | 7/2000 |

(Continued)

OTHER PUBLICATIONS

Y. Du, S. Honda, A. Taga, W. Liu, S. Suzuki, A novel Polybrene/Chondroitin Sulfate C Double Coated Capillary and Its Application in Capilarry Electrophoresis, Chinese Journal of Chemistry, (2002), 20, 1557-1565.*

(Continued)

*Primary Examiner* — J. Christopher Ball
*Assistant Examiner* — Maris R Kessel
(74) *Attorney, Agent, or Firm* — Wenderoth, Lind & Ponack, L.L.P.

(57) ABSTRACT

An object of the present invention is to provide a method for measuring hemoglobin that enables short-time, high-accuracy measurement of hemoglobin, in particular stable hemoglobin A1c, which is used as a diagnostic indicator of diabetes mellitus, and an electrophoresis apparatus that is suitably used in this measurement method. The present invention provides a method for measuring hemoglobins using electrophoresis, which includes: using a migration path having an inner surface coated with a cationic substance to be immobilized on the inner surface or a migration path having an inner surface made of a cationic material; and using a buffer solution containing a water-soluble polymer having an anionic group as an electrophoresis buffer solution.

11 Claims, 7 Drawing Sheets

(56) References Cited

U.S. PATENT DOCUMENTS

| | | | |
|---|---|---|---|
| 2003/0102215 A1* | 6/2003 | Bukshpan et al. | ............ 204/459 |
| 2004/0031683 A1 | 2/2004 | Eipel et al. | |
| 2007/0178240 A1 | 8/2007 | Yamazaki et al. | |

FOREIGN PATENT DOCUMENTS

| | | |
|---|---|---|
| EP | 1 548 429 | 6/2005 |
| EP | 1 889 918 | 2/2008 |
| EP | 2 144 055 | 1/2010 |
| EP | 2 144 056 | 1/2010 |
| EP | 2 144 057 | 1/2010 |
| EP | 2 148 193 | 1/2010 |
| JP | 2-159563 | 6/1990 |
| JP | 9-105739 | 4/1997 |
| JP | 9-510792 | 10/1997 |
| JP | 10-502175 | 2/1998 |
| JP | 10-512371 | 11/1998 |
| JP | 11-509320 | 8/1999 |
| JP | 2000-146910 | 5/2000 |
| JP | 2001-99838 | 4/2001 |
| JP | 2001/506364 | 5/2001 |
| JP | 2001-264336 | 9/2001 |
| JP | 2004-77305 | 3/2004 |
| JP | 2004/514136 | 5/2004 |
| JP | 2005-291926 | 10/2005 |
| JP | 2006-61019 | 3/2006 |
| JP | 2008-529006 | 7/2008 |
| WO | 96/23220 | 8/1996 |
| WO | 97/03351 | 1/1997 |
| WO | 01/35088 | 5/2001 |
| WO | 01/56771 | 8/2001 |
| WO | 2004/031757 | 4/2004 |
| WO | 2005/103670 | 11/2005 |
| WO | 2006/110725 | 10/2006 |
| WO | 2006/118306 | 11/2006 |

OTHER PUBLICATIONS

Jeffrey Ambler, Borek Janik, and Geoffrey Walker, Measurement of Glycosylated Hemoglobin on Cellulose Acetate Memberanes by Mobile Infinity Electrophoresis, Clinical Chemistry, vol. 29, No. 2 340-343 (1983).*
B. Y. Gong, J. W. Ho, Effect of zwitterionic surfactants on the separation of proteins by capillary electrophoresis, Electrophoresis, 18, 732-735 (1997).*
J. T. Smith, Z. E. Rassi, Capillary zone electrophoresis of biological substances with fused silica capillaries having zero or constant electroosmotic flow, Electrophoresis, 396-406 (1993).*
M. Mosely, L.J. Deterding, K.B. Tomer, J. W. Jorgenson, Determination of Bioactive Peptides Using Capillary Zone Electrophoresis/ Mass Spectrometry, Anal. Chem. 1991, 63, 109-114 (1991).*
Third party observations for counterpart EP Application No. 07860211.7 dated Dec. 3, 2010.
Office Action issued in counterpart EP Application No. 07860211.7 dated May 6, 2011.
K. Srinivasan et al. "Cross-Linked Polymer Coating for Capillary Electrophoresis and Application to Analysis of Basis Proteins, Acidic Proteins, and Inorganic Ions", Analytical Chemistry, vol. 69, No. 14, pp. 2798-2805, Jul. 15, 1997.
O.V. Krokhin et al., "New High-Performance Techniques for Ion-Exchange Separation", Journal of Analytical Chemistry, vol. 57, No. 10, pp. 920-927, 2002.
H. Shimomura et al., "Evaluation of Diabetes Mellitus Testing System (Kyoto Daiichi Kagaku) as DM Station", The Journal of Clinical Laboratory Instruments and Reagents, vol. 21, No. 3, pp. 303-308, 1998 (partial translation).
Catalog of Diabetes Testing System (partial translation).
Partial Translation of "Capillary Electrophoresis—Principles and Applications—" Second printing, published on Aug. 10, 1998 by Kodansha Ltd.
Office Action issued Jun. 18, 2013 in European Patent Application No. 07 860 211.7.
Partial European Search Report issued Jun. 14, 2013 in European Patent Application No. 13165825.4.
Michael J. Pugia et al., "Microfluidic Tool Box as Technology Platform for Hand-Held Diagnostics", Clinical Chemistry, vol. 51, No. 10, 2005, pp. 1923-1932, XP055065243.
European Office Action dated Jul. 10, 2014 issued in counterpart European Patent Application No. 13165825.4.
Extended European Search Report issued Sep. 25, 2013 in corresponding European Application No. 13165825.4.
Zangmeister R et al., UV Graft Polymerization of Polyacrylamide Hydrogel Plugs in Microfluidic Channels. Chemical Science and Technology and Laboratory. May 8, 2003, pp. 6901-6904.
Supplementary European Search Report issued Mar. 4, 2010 in European Application No. 07 86 0211.7.
H. Siren et al., "Direct Monitoring of Glycohemoglobin $A_{1c}$ in the Blood Samples of Diabetic Patients by Capillary Electrophoresis Comparison with an Immunoassay Method", Journal of Chromatography A, vol. 979, No. 1-2, pp. 201-207, Dec. 6, 2002.
C. J. A. Doelman et al., "Capillary Electrophoresis System for Hemoglobin $A_{1c}$ Determinations Evaluated", Clinical Chemistry, vol. 43, No. 4, pp. 644-648, Apr. 1, 1997.

\* cited by examiner

HEMOGLOBIN MEASUREMENT METHOD AND ELECTROPHORESIS APPARATUS

This application is a U.S. national stage of International Application No. PCT/JP2007/074982 filed Dec. 26, 2007.

TECHNICAL FIELD

The present invention relates to a method for measuring hemoglobin that enables short-time, high-accuracy measurement of hemoglobin, in particular stable hemoglobin A1c, which is used as a diagnostic indicator of diabetes mellitus, and an electrophoresis apparatus that is suitably used in this measurement method.

BACKGROUND ART

Hemoglobin (Hb), in particular hemoglobin A1c (hereinafter, also referred to as HbA1c) of a form of glycosylated hemoglobins reflects an average blood sugar level in past 1 to 2 months. Therefore, hemoglobin A1c is widely used in a screening test for diabetes mellitus and as a test item for checking whether a diabetic keeps the blood sugar under control.

Conventionally, HbA1c has been measured by HPLC, immunoassay, electrophoresis or the like. Especially, HPLC is widely used in clinical examinations. HPLC requires only 1 to 2 minutes to measure each sample, and has achieved a measurement accuracy of about 1.0% in terms of a CV value obtained by a within-run reproducibility test. Measurement methods used for checking whether a diabetic keeps the blood sugar under control are required to perform at this level.

Meanwhile, application of an electrophoresis technique that enables high-accuracy measurement of HbA1c to the clinical examinations is expected to yield a significantly advantageous effect in cost because an electrophoresis apparatus has a simple configuration, and can be formed as a low-cost small system such as a microdevice electrophoresis system.

Measurement of Hb by electrophoresis has been used for a long time to separate abnormal Hbs with an unusual amino acid sequence. However, separation of HbA1c is significantly difficult, and takes 30 minutes or more by gel electrophoresis. Thus, electrophoresis has been unsatisfactory in terms of measurement accuracy and measurement time when applied to the clinical examinations. Therefore, electrophoresis has hardly been applied to clinical diagnosis of diabetes mellitus.

However, capillary electrophoresis, which was proposed in around 1990, generally enables high-accuracy measurement with high separation efficiency. For example, Patent Document 1 discloses a method for separating HbA1c by capillary electrophoresis.

However, use of the method of Patent Document 1 does not overcome the problem of taking a long time to measure, and also may denature Hb due to use of a buffer solution with a high pH of 9 to 12. For these reasons, it has been difficult to apply this method to the clinical examinations.

Patent Document 2 discloses a method using capillary electrophoresis in which an ionic polymer is allowed to flow through a capillary to dynamically coat the inner surface of the capillary with the ionic polymer, and a buffer solution containing a sulfated polysaccharide is used. This method enables measurement in a shorter time compared to gel electrophoresis, and takes only about 10 minutes to measure.

However, the coating layer formed by such a dynamic coating technique is significantly altered by each sample measurement, and this alteration prevents measurement of another sample without performing required procedure. In order to coat the inside of the capillary in the same way at the beginning of each measurement, it is necessary to remove the remaining coating layer by washing after each measurement, and to carry out the coating procedure again. Namely, for repetitive measurement, the washing and coating procedure needs to be performed between each measurement, resulting in an increase in the measurement time. The washing and coating procedure may cause a measurement error, and in addition requires a coating reagent to be prepared for the measurement, leading to a disadvantage in cost. Even when not used for the repetitive measurement, the technique takes about 10 minutes to measure, which is much longer than needed in HPLC, and is unsatisfactory for application to the clinical examinations.

For clinical diagnosis of diabetes mellitus, stable HbA1c, which is a type of HbA1c and used as a diabetic indicator, should be separated to remove effects of modified Hbs such as unstable HbA1c, carbamylated Hbs and acetylated Hbs. However, electropherograms obtained by the methods disclosed in Patent Document 1 and Patent Document 2 were unsatisfactory in terms of separation performance and measurement accuracy, and it has been difficult to separate stable HbA1c by the techniques within the scope of these methods.

Patent Document 1: Japanese Kohyo Publication No. Hei-09-510792(JP-T 09-510792)

Patent Document 2: Japanese Kokai Publication No. Hei-09-105739(JP-A 09-105739)

DISCLOSURE OF THE INVENTION

Problems to be Solved by the Invention

In view of the above-mentioned state of the art, the present invention aims to provide a method for measuring hemoglobin that enables short-time, high-accuracy measurement of hemoglobin, in particular stable hemoglobin A1c, which is used as a diagnostic indicator of diabetes mellitus, and an electrophoresis apparatus that is suitably used in this measurement method.

Means for Solving the Problems

The present invention provides a method for measuring hemoglobin using electrophoresis, which includes: using a migration path having an inner surface coated with a cationic substance to be immobilized on the inner surface or a migration path having an inner surface made of a cationic material; and using a buffer solution containing a water-soluble polymer having an anionic group as an electrophoretic buffer solution, and also provides an electrophoresis apparatus suitably used in the measurement method.

Hereinafter, the present invention is described in detail.

The present inventors conducted intensive studies to find out that a method for measuring hemoglobin using electrophoresis in which a migration path having an inner surface coated with a cationic substance to be immobilized on the inner surface or a migration path having an inner surface made of a cationic material, and a buffer solution containing a water-soluble polymer having an anionic group are used for electrophoresis enables short-time, high-accuracy measurement. Thus, the present inventors completed the present invention. In addition, the present inventors found a structure and conditions of an electrophoresis apparatus provided with a small low-cost microdevice suitably used in the above-mentioned measurement method, and thus completed the present invention.

In the method for measuring hemoglobin of the present invention, a migration path having an inner surface coated with a cationic substance to be immobilized on the inner surface or a migration path having an inner surface made of a cationic material is used. The migration path having the cationic inner surface avoids non-specific adsorption of measurement components and the like, and enables high-accuracy measurement. Unlike the dynamic coating technique, the measurement method of the present invention can avoid procedure such as the coating procedure and the washing procedure to be carried out after each measurement, and thereby enables short-time measurement. In addition, the measurement method of the present invention is significantly advantageous in terms of cost because the measurement method of the present invention does not need a coating reagent provided in a measurement system. The measurement method of the present invention enables separation of stable hemoglobin A1c from abnormal hemoglobins and the like, which is impossible in the dynamic coating technique, and also performs with remarkably improved measurement accuracy compared to the dynamic coating technique.

The migration path is defined as a path in which a measurement sample is moved and/or separated by electrophoresis (a path from a position at which a sample is injected to a position at which components of the sample are detected). Specific examples are as follows: In capillary electrophoresis, the migration path is defined as a part of a capillary from a position at which a sample is injected to a position at which components of the sample are detected by a detector. In microdevice electrophoresis, the migration path is defined as a part of a flow channel on a microdevice from a position at which a sample is injected to a position at which components of the sample are detected by a detector in a microdevice electrophoresis apparatus.

Specifically, the inner surface of the migration path is defined, for example, in capillary electrophoresis, as the inner surface of the migration path of the capillary, and in microdevice electrophoresis, as the inner surface of the migration path of the flow channel on the microdevice in the microdevice electrophoresis apparatus.

The migration path used in the measurement method of the present invention is (1) a migration path having an inner surface coated with a cationic substance to be immobilized on the inner surface, or (2) a migration path having an inner surface made of a cationic material.

First, (1) the migration path having the inner surface coated with a cationic substance to be immobilized on the inner surface is described in more detail.

The immobilized coating refers to coating in which a coating agent is permanently adsorbed on the surface of a material forming the inner surface of the migration path such as glass (borosilicate glass, quartz, etc.), silica (fused silica, polydimethylsiloxane, etc.), metals, and resins (polyacrylic resins, polystyrenic resins, polylactic acid resins, polycarbonate resins, olefinic resins, etc.) by an interaction between the material of the migration path and the coating agent such as an ionic interaction or hydrophobic interaction, or coating in which the both are linked to each other by a covalent bond.

The above-mentioned interaction and covalent bond are highly stable, and do not undergo in usual measurement or the washing procedure a change which affects measured values. Unlike the dynamic coating technique in which the coating agent adsorbing on the material of the migration path in equilibrium state is regarded as a quasi-coating layer, the immobilized coating enables repetitive measurement without reperforming the coating procedure. In addition, the immobilized coating avoids the coating procedure to be performed immediately before measurement, and allows the migration path to be stored for a long period of time.

A surface alteration treatment may be performed on the surface of the migration path for the purpose to more firmly immobilize the immobilized coating.

The surface alteration treatment is not particularly limited, and examples thereof include optical treatments such as ultraviolet exposure and plasma treatment; chemical treatments such as reaction and bond with a chemical substance of any type; coating treatments using a compound or polymer of any type, or the like; conventionally known chemical denaturation treatments and/or physical denaturation treatments; and other treatments.

More specifically, desirable examples of the immobilized coating method include (a) a method in which the inner surface of the migration path is coated with a cationic polymer to be immobilized thereon, and (b) a method in which a low-molecular-weight hydrophilic compound having a cationic group is linked to the inner surface of the migration path by a covalent bond.

First, the method (a) in which the inner surface of the migration path is coated with a cationic polymer to be immobilized thereon is described.

The cationic polymer used herein is a polymer having a cationic group in the polymer. The cationic group is not particularly limited, and examples thereof include primary, secondary and tertiary amino groups, quaternary ammonium group, and the like. The cationic polymer is desirably hydrophilic.

The cationic polymer is not particularly limited, and examples thereof include aminated polysaccharides, organic synthetic polymers having an amino group, and the like.

The aminated polysaccharides are not particularly limited, and examples thereof include known aminated polysaccharides, and the like. Examples of the known aminated polysaccharides include chitosan derivatives such as chitin and chitosan, and salts thereof; N-substituted cellulose derivatives such as aminocellulose and N-methylaminocellulose, and salts thereof; compounds for introducing an amino group to a neutral polysaccharide such as dextran, agarose, mannan or starch, or a derivative thereof, and salts thereof; and other known aminated polysaccharides.

The organic synthetic polymers having an amino group are not particularly limited, and examples thereof include known organic synthetic polymers having an amino group, and the like. Examples of the known organic synthetic polymers having an amino group include polyethyleneimine, polybrene, and poly(meth)acrylates having an amino group such as poly 2-diethylaminoethyl (meth)acrylate and polyacrylamide, copolymers thereof, and the like.

The desirable lower limit of the weight average molecular weight of the cationic polymer is 500. In the case where the weight average molecular weight of the cationic polymer is less than 500, it is difficult to sufficiently coat the inner surface of the migration path, possibly leading to poor hemoglobin separation performance.

A method for immobilizing the cationic polymer on the migration path is not particularly limited, and a conventionally known method can be used. Examples thereof include a method in which the cationic polymer is allowed to contact the inner surface of the migration path and to physically adsorb on the inner surface of the migration path by a hydrophobic or electrostatic interaction or the like and thus immobilized thereon; a method in which the cationic polymer is immobilized on the inner surface of the migration path by a covalent bond between respective functional groups of the inner surface and the cationic polymer, or a covalent bond via another substance and the like; and other methods. Specific examples include a method in which a solution containing the cationic polymer is allowed to flow through the inside of the migration path, air is injected into the migration path to send out the solution, and then processes such as heating and drying are repeatedly performed; and other methods. The cationic polymer immobilized by these methods through the processes such as the heating and drying processes is less likely to peel off, and allows repetitive measurement.

The cationic polymer to be immobilized on the migration path is desirably provided, although depending on the type of the cationic polymer or the immobilization method, as a cationic polymer solution in the immobilization method.

The desirable lower limit of the concentration of the cationic polymer solution is 0.01%, and the desirable upper limit thereof is 20%. In the case where the concentration of the cationic polymer solution is less than 0.01%, the cationic polymer may be insufficiently immobilized. On the other hand, in the case where the concentration of the cationic polymer is more than 20%, the formed layer of the cationic polymer is uneven and may peel off during measurement of hemoglobin, which in turn may cause low repeatability.

The immobilized coating layer may be any structure as long as the cationic polymer is immobilized to form the innermost surface of the migration path. However, the immobilized coating layer desirably include a non-ionic hydrophilic polymer immobilized between the inner surface of the migration path and the cationic polymer layer, because this structure makes it possible to effectively prevent non-specific adsorption during electrophoresis, reduction in the separation performance due to electroosmotic flow, and the like.

Thus, in this coating method, the inner surface of the migration path is coated with the non-ionic hydrophilic polymer to be immobilized on the inner surface, and additionally the obtained non-ionic hydrophilic polymer layer is coated with the cationic polymer to be immobilized on the non-ionic hydrophilic polymer layer.

The non-ionic hydrophilic polymer is not particularly limited, and desirable examples thereof include hydrophilic polymers without ion exchange groups. Specifically, for example, a polymer having a non-ionic hydrophilic group such as hydroxyl group, glycol group and epoxy group without ion exchange groups in its structure is desirable.

The non-ionic hydrophilic polymer is not particularly limited, and examples thereof include non-ionic polysaccharides, non-ionic organic synthesis polymers, and the like.

The non-ionic polysaccharides are not particularly limited, and examples thereof include polysaccharides such as cellulose, dextran, agarose, mannan and starch, derivatives and mixtures thereof.

The non-ionic organic synthesis polymers are not particularly limited, and examples thereof include water-soluble polymers such as polyethylene glycol, polypropylene glycol, polyvinyl alcohol, and polyvinyl pyrrolidone; and polymers and copolymers obtained by polymerizing acrylic monomers such as 2-hydroxyethyl (meth)acrylate, 2-hydroxypropyl (meth)acrylate, polyethylene glycol (meth)acrylate, polypropylene glycol (meth)acrylate, glycerol (meth)acrylate, and glycidyl (meth)acrylate, salts, derivatives thereof and/or the like.

The non-ionic hydrophilic polymer may be a mixture or copolymer of the above-mentioned materials, or a copolymer of the above-mentioned materials and materials not listed above.

Next, the method (b) in which a low-molecular-weight hydrophilic compound having a cationic group is linked to the inner surface of the migration path by a covalent bond is described.

In this case, the surface of the migration path is required to have a structure that allows the hydrophilic compound to be linked to the surface of the migration path by a covalent bond forming reaction (hereinafter, also referred to as "a covalently bondable structure").

The covalently bondable structure is not particularly limited as long as it can form a covalent bond by a conventionally known chemical reaction. Examples thereof include structures or substances having a group such as hydroxyl group, carboxyl group, sulfonic acid group, amino group, ester group, ether group, epoxy group, halogen group, imino group, imidazole group, silanol group, and trialkoxysilyl group, and other structures or substances.

The migration path may be originally made of a material having the above-mentioned covalently bondable structure, or may be subjected to the above-mentioned surface alteration treatment to obtain the surface having the covalently bondable structure. Especially, the migration path originally made of a material having the covalently bondable structure is desirably used.

The migration path having such a covalently bondable structure is linked to the hydrophilic compound having a cationic group by a covalent bond.

The hydrophilic compound having a cationic group used herein is a compound having a cationic hydrophilic group in its structure.

The cationic hydrophilic group is not particularly limited, and examples thereof include onium groups such as primary, secondary and tertiary amino groups, quaternary ammonium group, imide group, guadinino group, and phosphonium group, and the like. Especially, primary, secondary and tertiary amino groups are more desirable, and primary and secondary amino groups are further more desirable.

The desirable lower limit of the molecular weight of the hydrophilic compound having a cationic group is 20, and the desirable upper limit thereof is 800. A hydrophilic compound having a molecular weight of less than 20 produces only a small hydrophilizing effect, and therefore may be less likely to prevent non-specific adsorption. When a hydrophilic compound having a molecular weight of more than 800 is linked to the surface of the migration path, hemoglobins may be insufficiently separated, possibly leading to low measurement accuracy. Electropherograms obtained by, in particular, long-time repetitive measurement may have deformed peaks, possibly resulting in inaccurate measurement. The more desirable lower limit is 30, and the more desirable upper limit is 500.

The hydrophilic compound having a cationic group may have a repetitive structure such as dimer and trimer as long as its molecular weight is 800 or less.

The hydrophilic compound having a cationic group has a structure that allows the surface of the migration path having the covalently bondable structure to be linked to the hydrophilic compound by a covalent bond formation reaction (hereinafter, also referred to as "covalently bondable structure"). The above-mentioned covalently bondable structure of the hydrophilic compound allows formation of a covalent bond with the covalently bondable structure of the surface of the migration path, which in turn allows the hydrophilic compound to be firmly linked to the surface of the migration path.

The covalently bondable structure is not particularly limited, and examples thereof include structures that can form a covalent bond by a conventionally known chemical reaction, and other structures. Specific examples include the same covalently bondable structures as those of the surface of the migration path.

The hydrophilic compound having a cationic group is not particularly limited, and examples thereof include urea derivatives such as urea, and salts, substitution products and polymers thereof; aminoalkanes such as methylamine, dimethylamine, trimethylamine, ethylamine, diethylamine, triethylamine, propylamine, dipropylamine, isopropylamine, diisopropylamine, tributylamine, methylaminopropylamine, dimethylaminopropylamine glycidylaminopropylamine, and diethanolaminopropylamine, and derivatives, salts, substitution products and polymers thereof, and the like; diaminoalkanes such as ethylenediamine, propylenediamine, tetramethylendiamine, 1,3-propanediamine, hexamethylenediamine, and hydrazino group propanediamine, and derivatives, salts, substitution products and polymers thereof, and the like; alkanolamines such as monoethanolamine, diethanolamine, triethanolamine, monoisopropanolamine, diisopropanolamine, triisopropanolamine dimethylmethanolamine, and diethylmethanolamine, and derivatives, salts, substitution products and polymers thereof, and the like; amino acids such as lysine, arginine, glutamine, ornithine, γ-aminobutyric acid, and 3-aminoalanine, and derivatives, salts, substitution products and polymers thereof, and the like; imines and imides such as guanidine, aminoguanidine, biguanide, and trimethyleneimine, and derivatives, salts, substitution products and polymers thereof, and the like; amino group-containing silane coupling agents such as 3-aminopropyltriethoxysilane, 3-(2-aminoethyl)aminopropyltrimethoxysilane, 3-(2-aminoethyl)aminopropylmethyldimethoxysilane, aminosilane, and 3-aminopropyltrimethoxysilane, and derivatives, salts, substitution products and polymers thereof. Especially, aminoalkanes, diaminoalkanes, and the silane coupling agents are more desirable.

A combination of the covalently bondable structure of the hydrophilic compound having a cationic group and the covalently bondable structure of the surface of the migration path is not particularly limited as long as they can react to form a covalent bond. The covalently bondable structure of the hydrophilic compound having a cationic group and the covalently bondable structure of the surface of the migration path may be the same or different.

The covalently bondable structure of the surface of the migration path and the covalently bondable structure of the hydrophilic compound having a cationic group desirably react with each other directly to form a covalent bond. However, the hydrophilic compound having a cationic group and the surface of the migration path may be linked to each other via a compound having functional groups that can react with the covalently bondable structure of the hydrophilic compound having a cationic group and the covalently bondable structure of the surface of the migration path to form covalent bonds with both (hereinafter also referred to as a spacer), that is, may be indirectly linked to each other.

The spacer has at least a functional group that can react with the covalently bondable structure of the hydrophilic compound having a cationic group to form a covalent bond, and a functional group that can react with the covalently bondable structure of the surface of the migration path to form a covalent bond. Namely, any spacer may be used as long as it has two or more of the covalently bondable structures in one molecule. The two or more covalently bondable structures of the spacer may be structures of the same type or different types.

Specific examples of the spacer include carbodiimides having imide groups; aminocarboxylic acids having an amino group and a carboxyl group; alkylmethylenediamines having amino groups; epihalohydrins having halogen groups such as epichlorohydrin; diglycidyl ether; diepoxides such as diepoxide; and other spacers.

In the method for measuring hemoglobin of the present invention, when the hydrophilic compound having a cationic group and the surface of the migration path are linked to each other via the spacer, the sum of the molecular weights of the spacer and the hydrophilic compound having a cationic group is desirably 20 to 800.

The hydrophilic compound having a cationic group may be linked only to form the innermost surface of the migration path, or may be linked to form the innermost surface of the migration path and the innermost surface of the flow channel except the migration path as long as it is linked by a covalent bond to form the innermost surface of the migration path.

A method for linking the hydrophilic compound having a cationic group to the surface of the migration path by a covalent bond is not particularly limited. The hydrophilic compound having a cationic group may be reacted under conventionally known reaction conditions determined according to the type of the hydrophilic compound. Specific examples include a method in which a solution containing the hydrophilic compound is allowed to flow through the inside of the migration path to contact the surface of the migration path and to react under suitable reaction conditions, and other methods.

Optionally, an activation treatment of the functional groups may be performed, and processes such as heating and drying may be performed during or after the reaction.

When the solution containing the hydrophilic compound having a cationic group is allowed to flow through the inside of the migration path to contact the surface of the migration path and to react, the desirable lower limit of the concentration of the solution containing the hydrophilic compound having a cationic group is 0.1% by weight, and the desirable upper limit thereof is 30% by weight. A solution containing the hydrophilic compound having a cationic group at a concentration of 0.1% or less is less likely to produce an effect of the linkage of the hydrophilic compound having a cationic group by a covalent bond due to the insufficient concentration. A solution containing the hydrophilic compound having a cationic group at a concentration of 30% by weight or more, although depending on the type of the hydrophilic compound, may be handled with difficulty and cause problems such as clogging of a reaction product in the migration path.

Next, the other migration path used in the present invention, that is, (2) the migration path having an inner surface made of a cationic material is described.

"A migration path made of a cationic material" used herein is a migration path formed using a cationic material by any known molding or processing method. Therefore, a cationic migration path in which the inner surface is altered by any conventional techniques or the coating methods disclosed herein to show a cationic property is not encompassed. Namely, "the migration path made of a cationic material" means a migration path with a cationic property derived from the original structure of the material prior to being formed into the migration path without being subjected to any procedure of the dynamic coating method and the immobilized coating method.

The cationic material has a cationic group in its structure, and the cationic group shows a cationic property under running conditions of electrophoresis.

The cationic group is not particularly limited, and examples thereof include primary, secondary and tertially amino groups, quaternary ammonium group, pyridium group, guadinino group, functional groups containing these groups, and the like. Especially, primary, secondary and tertially amino groups and quaternary ammonium group are desirable.

Although the cationic material is not particularly limited, a polymer material having the above-mentioned cationic group is desirable.

A method for preparing the polymer material having the cationic group is not particularly limited, and examples thereof include a method in which monomers each having the cationic group are polymerized; a method in which the cationic group is introduced into a polymer material serving as a base material; and other methods. Especially, the method in which monomers each having the cationic group are polymerized is desirable.

The material having the cationic group is desirably hydrophilic.

The monomer having the cationic group is not particularly limited, and examples thereof include (meth)acrylamides; alkyl(meth)acrylamides such as methyl(meth)acrylamide, dimethyl(meth)acrylamide, ethyl(meth)acrylamide, ethylhexyl(meth)acrylamide, and N-isopropyl(meth)acrylamide; alkylaminoalkyl(meth)acrylamides such as methylaminoethyl(meth)acrylamide, diethylaminopropyl(meth)acrylamide, dimethylaminohydroxypropyl(meth)acrylamide, and N-tert-butyl(meth)acrylamide; alkylamino(meth)acrylates such as methylamino(meth)acrylate, and ethylamino(meth)acrylate; dialkylaminoalkyl(meth)acrylates such as dimethylaminoethyl(meth)acrylate, diethylaminoethyl(meth)acrylate, and diethylaminopropyl(meth)acrylate; trimethylammoniums such as (meth)acrylamidepropyl trimethylammonium chloride, (meth)acryloyloxyethyltrimethylammonium chloride, (meth)acryloyloxy-2-hydroxypropyltrimethylammonium chloride, and (meth)acryloylaminopropyltrimethylammonium chloride; allyl compounds such as allylamine, allylamine amide, diallylamine, dimethylallylamine, diallyldimethylammonium chloride, diallyl(meth)acrylamide, and diallylalkyl(meth)acrylamide; imines such as ethyleneimine, trimethyleneimine, and tetramethylenimine; vinylamine; vinylpyrrolidone; amino acids such as ornithine, and lysine; quarternary ammonium salts of mono-halides of these monomers; and the like.

One type of the monomers having the cationic group may be used alone, or two or more types of these may be used in combination. Alternatively, they may be used as a copolymer in combination with monomers not listed above.

In the method for measuring hemoglobin of the present invention, the migration path, the flow channel and the device except the inner surface of the migration path may be made of the cationic material, or may be made of a material other than the cationic material as long as the inner surface of the migration path is made of the cationic material.

Additionally, the inner surface of the migration path used in the method for measuring hemoglobin of the present invention is desirably ozonized. Ozonization of the inner surface of the migration path coated with the immobilized cationic substance or ozonization of the inner surface of the migration path made of the cationic material makes it possible to hydrophilize even slightly-hydrophobic portions. Such hydrophilization makes it possible to prevent non-specific adsorption of components, such as proteins and lipids, contained in a human blood sample flowing through the inside of the migration path, and to sufficiently separate and measure target hemoglobins.

The ozonization is not particularly limited, and examples thereof include an ozone gas treatment, an ozone water treatment, and the like. A method for performing the ozone gas treatment is not particularly limited, and examples thereof include a method in which ozone gas is allowed to contact the migration path. A method for performing the ozone water treatment is not particularly limited, and examples thereof include a method in which ozone water is allowed to contact the migration path. Especially, the ozone water treatment is desirable.

Although the concentration of ozone gas dissolved in ozone water used in the ozone water treatment is not particularly limited, the desirable lower limit thereof is 20 ppm. Ozone water containing ozone gas at a concentration of less than 20 ppm may require a longer time to complete ozonization, or fail to sufficiently prevent non-specific adsorption of target measurement substances and the like. The more desirable lower limit is 50 ppm.

The migration path may be further coated with the cationic substance to be immobilized thereon after the ozonization. Even when the ozonization is followed by immobilized coating with the cationic substance, the effect of the ozonization performed a priori is preserved.

The migration path used in the method for measuring hemoglobin of the present invention is desirably filled with an ion exchanger. The inside of the migration path may be entirely filled with the ion exchanger, or the inside of the migration path may be partially filled with the ion exchanger.

When a sample is introduced into the migration path filled with the ion exchanger, hemoglobins contained in the sample are moved by electrophoresis and contact the ion exchanger to be separated into each type. Therefore, it is possible to detect each separated substance with a detector. The ion exchanger used herein is an insoluble carrier having an ion exchange group.

The ion exchanger is not particularly limited, and examples thereof include insoluble polymers having an ion exchange group.

The ion exchange group is not particularly limited, and examples thereof include cation exchange groups such as carboxyl group, phosphate group, and sulfonic acid group; and anion exchange groups such as amino group.

A polymer skeleton of the polymers having an ion exchange group is not particularly limited, and examples thereof include organic polymers such as organic synthesis polymers and polysaccharides; inorganic polymers such as silica based polymers and ceramic polymers; and the like.

The ion exchanger may be crosslinked or may not be crosslinked as long as it is an insoluble particle during electrophoresis. However, the ion exchanger is desirably crosslinked.

The ion exchanger may be a polymer obtained by polymerizing monomers each having the above-mentioned ion exchange group, or a polymer obtained by preparing a polymer and introducing the ion exchange group into the polymer. The polymer obtained by polymerizing monomers each having the ion exchange group is desirable.

Since samples used in the method for measuring hemoglobin of the present invention are blood, it is necessary to prevent non-specific adsorption of components in the samples on the ion exchanger. Therefore, the ion exchanger is desirably hydrophilic. More specifically, for example, ion exchangers made of a hydrophilic material and ion exchangers of a hydrophilized polysaccharide, a hydrophilized organic synthesis polymer, hydrophilized silica, or the like are desirable, and ion exchangers of a hydrophilic organic synthesis polymer are more desirable.

Polysaccharides used as the ion exchanger are not particularly limited, and examples thereof include insoluble compounds of polysaccharides containing a cationic group, and the like. Examples of the polysaccharides containing a cationic group include chitosan derivatives such as chitin and chitosan, and salts thereof; N-substituted cellulose derivatives such as aminocellulose and N-methylaminocellulose, and salts thereof; compounds for introducing an amino group to a neutral polysaccharide such as dextran, agarose, mannan, or starch, or a derivative thereof, and salts thereof; and other polysaccharides containing a cationic group. Other examples include insoluble compounds of known polysaccharides containing an anionic group, and the like. Examples of the known polysaccharides containing an anionic group include polysaccharides containing a sulfonic acid group such as chondroitin sulfate, dextran sulfate, heparin, heparan and, fucoidan, and salts thereof; polysaccharides containing a carboxyl group such as alginic acid and pectic acid, and salts thereof; compounds for introducing an anionic group to a neutral polysaccharide such as cellulose, dextran, agarose, mannan, or starch, or a derivative thereof, and salts thereof; and other known polysaccharide containing an anionic group.

The above-mentioned ion exchangeable polysaccharides may be used in a form of a mixture with a neutral polysaccharide such as starch, dextran, agarose, or mannan, or a substance bound to the neutral polysaccharide.

The organic synthesis polymers used as the ion exchanger are not particularly limited, and examples thereof include organic synthesis polymers obtained by polymerizing the monomers each having the ion exchange group alone; organic synthesis polymers obtained by copolymerizing the monomers each having the ion exchange group, and other hydrophilic monomers without the ion exchange group; and other organic synthesis polymers. Specifically, for example, acrylic polymers obtained by polymerizing acrylic monomers are desirable.

The monomer having the ion exchange group is not particularly limited, and examples thereof include monomers having a carboxyl group such as (meth)acrylic acid; monomers having a sulfonic acid group such as 2-acrylamide-2-methylpropanesulfonic acid; monomers having an amino group such as 2-diethylaminoethyl (meth)acrylate; and other monomers having the ion exchange group. In addition, glycidyl(meth)acrylate may be used through substitution of the glycidyl group by a carboxyl group, a sulfonic acid group or the like after polymerization. Alternatively, an insoluble compound of polyethyleneimine or polybrene that has an amino group, or the like can also be used.

The hydrophilic monomer without the ion exchange group is not particularly limited, and examples thereof include 2-hydroxyethyl(meth)acrylate, polyethyleneglycol di(meth)acrylate, polymethylol alkane poly(meth)acrylate, (meth)acrylamide, glycidyl(meth)acrylate, and the like. Alternatively, an insoluble compound of polyvinyl alcohol, polyvinylpyrrolidone or polyethyleneglycol, or the like can also be used.

The shape of the ion exchanger is not particularly limited, and examples thereof include sphere, crushed shapes, and other shapes. Especially, sphere is desirable, and perfect sphere or a shape close to perfect sphere is more desirable.

The size of the ion exchanger is not particularly limited as long as it can be charged into the migration path. However, the desirable lower limit of the diameter is 0.1 μm, and the desirable upper limit is 30 μm. An ion exchanger having a diameter of less than 0.1 μm forms too small voids, and thereby makes it difficult for a sample to travel, possibly leading to insufficient electrophoresis performance. An ion exchanger having a diameter of more than 30 μm forms too large voids, and thereby causes insufficient interaction between the sample and the ion exchanger, possibly leading to poor separation performance.

The more desirable lower limit is 1 μm, and the more desirable upper limit is 20 μm.

In the method for measuring hemoglobin of the present invention, a buffer solution containing a water-soluble polymer having an anionic group is used as an electrophoresis buffer solution.

The electrophoresis buffer solution (hereinafter, also simply referred to as "buffer solution") used herein includes (A) a buffer solution for filling the inside of the migration path for electrophoresis, (B) a buffer solution for filling an anode reservoir and cathode reservoir set for the ends of the migration path for electrophoresis, (C) a buffer solution for washing the inside of the migration path, (D) a hemolysing agent for dissolving and diluting a sample, and (E) other buffer solutions. In the method for measuring hemoglobin of the present invention, all these buffer solutions may contain the water-soluble polymer having an anionic group, or only some of the buffer solutions may contain the water-soluble polymer having an anionic group. At least the buffer solutions (A) and (B) desirably contain the water-soluble polymer having an anionic group.

Any buffer solutions can be used as long as the solutions contain a conventionally known buffer composition having buffer capacity. Specific examples thereof include solutions containing an organic acid such as citric acid, succinic acid, tartaric acid, or malic acid, a salt thereof, or the like; solutions containing an amino acids such as glycine, taurine or arginine; solutions containing an inorganic acid such as hydrochloric acid, nitric acid, sulfuric acid, phosphoric acid, boric acid or acetic acid, a salt thereof, or the like; and other solutions.

Optionally, a generally used additive may be added to the above-mentioned buffer solution. Examples the generally used additive include surfactants, various polymers, hydrophilic low-molecular-weight compounds, and the like.

The anionic group of the water-soluble polymer having an anionic group is not particularly limited, and examples thereof include conventionally known anionic groups such as carboxyl group, phosphate group, and sulfonic acid group. Especially, sulfonic acid group is desirable.

The water-soluble polymer having an anionic group may have two or more of the above-mentioned anionic groups in the polymer, or may have plural kinds of the above-mentioned anionic groups. The water-soluble polymer having an anionic group is completely dissolved in the buffer solution to be used. The desirable lower limit of the water solubility thereof is 1 g/L. A water-soluble polymer having an anionic group with a water solubility of less than 1 g/L may be less effective due to the low concentration, possibly leading to insufficient measurement accuracy. The more desirable lower limit is 5 g/L.

The water-soluble polymer having an anionic group is not particularly limited, and examples thereof include water-soluble polysaccharides having an anionic group, and water-soluble organic synthesis polymers having an anionic group.

The water-soluble polysaccharides having an anionic group is not particularly limited, and examples thereof include polysaccharides containing a sulfonic acid group such as chondroitin sulfate, dextran sulfate, heparin, heparan, and fucoidan, and salts thereof; polysaccharides containing a carboxyl group such as alginic acid, and pectic acid, and salts thereof; conventionally known polysaccharides having an anionic group such as compounds for introducing an anionic group to a neutral polysaccharide such as cellulose, dextran, agarose, mannan, or starch, and a derivative thereof, and salts thereof; and other water-soluble polysaccharides having an anionic group. Especially, sulfated polysaccharides such as chondroitin sulfate and dextran sulfate are suitable.

The water-soluble organic synthesis polymer having an anionic group are not particularly limited, and examples thereof include known water-soluble organic synthesis polymers containing an anionic group. Especially, water-soluble acrylic polymers having an anionic group, that is, polymers mainly composed of acrylic acid or methacrylic acid, or a derivative or an ester thereof, and the like are desirable.

Specific examples thereof include acrylic polymers obtained by polymerizing monomers having a carboxyl group such as (meth)acrylic acid and 2-(meth)acryloyloxyethyl succinic acid; acrylic polymers obtained by polymerizing monomers having a phosphate group such as ((meth)acryloyloxyethyl) acid phosphate, (2-(meth)acryloyloxyethyl) acid phosphate, and (3-(meth)acryloyloxypropyl) acid phosphate; acrylic polymers obtained by polymerizing monomers having a sulfonic acid group such as 2-(meth)acrylamide-2-methylpropanesulfonic acid, (meth)acrylamide propanesulfonic acid, sulfopropyl (meth)acrylate and (meth)acryloyloxynaphthalene sulfonic acid; and other water-soluble acrylic polymers having an anionic group. Especially, the acrylic polymers obtained by polymerizing monomers having a sulfonic acid group are suitable.

The acrylic polymer may be a copolymer of (meth)acrylic monomers having an anionic group and (meth)acrylic monomers without anionic groups.

The (meth)acrylic monomers without anionic groups are not particularly limited as long as the (meth)acrylic monomers can be copolymerized with the (meth)acrylic monomers having an anionic group. For example, non-ionic hydrophilic (meth)acrylic acid esters are desirable. Specific examples thereof include 2-hydroxyethyl(meth)acrylate, 2-hydroxypropyl(meth)acrylate, glycerol(meth)acrylate, glycidyl (meth)acrylate, polyethylene glycol (meth)acrylate, polypropylene glycol (meth)acrylate, and the like.

The amount of the (meth)acrylic monomer without anionic groups to be added is not particularly limited as long as the copolymer to be produced is water-soluble. However, the desirable upper limit is 1000 parts by weight with respect to 100 parts by weight of the (meth)acrylic monomer having an anionic group. When more than 1000 parts by weight of the (meth)acrylic monomer without anionic groups is added, the copolymer to be produced may be insoluble to water.

The desirable lower limit of the amount of the water-soluble polymer having an anionic group contained in the buffer solution is 0.01% by weight, and the desirable upper limit thereof is 10% by weight. In the case where the buffer solution contains less than 0.01% by weight of the water-soluble polymer having an anionic group, the effect of the water-soluble polymer addition is less likely to be produced, possibly leading to, for example, insufficient separation performance in the measurement of hemoglobin. In the case where the buffer solution contains more than 10% by weight of the water-soluble polymer having an anionic group, problems such as an increase in the measurement time and insufficient separation may occur.

The buffer solution desirably further contains a chaotropic compound.

The chaotropic compound used herein is a compound that characteristically breaks the interaction between water molecules, and reduces the hydrophobic interaction between hydrophobic molecules to increase the water solubility of the hydrophobic molecule.

The chaotropic compound is not particularly limited, and examples thereof include compounds containing an anionic chaotropic ions such as tribromoacetate ion, trichloroacetate ion, thiocyanate ion, iodide ion, perchlorate ion, dichloroacetate ion, nitrate ion, bromide ion, chloride ion, and acetate ion; compounds containing a cationic chaotropic ion such as barium ion, calcium ion, lithium ion, cesium ion, potassium ion, magnesium ion, and guanidine ion; urea compounds such as urea and thiourea; and other chaotropic compounds. Especially, the compounds containing a thiocyanate ion, a perchlorate ion, a nitrate ion, or a guanidine ion, the urea compounds, and the like are desirable.

The amount of the chaotropic compound to be added is not particularly limited. The desirable lower limit is 0.01% by weight, and the desirable upper limit is 30% by weight although these values vary depending on the type of the chaotropic compound. Addition of the chaotropic compound in an amount of less than 0.01% by weight may not deliver desired separation performance of hemoglobin, and the like. Addition of the chaotropic compound in an amount of more than 30% by weight may generate heat during electrophoresis, and causes problems such as deformed peaks in an obtained electropherogram. The more desirable lower limit is 0.05% by weight, and the more desirable upper limit is 20% by weight.

The chaotropic compound may be added to all the above-mentioned buffer solutions (A) to (E), or may be added only to some of the buffer solutions. The chaotropic compound is desirably added to at least the buffer solutions (A) and (B).

The buffer solutions desirably further contain a nitrite.

The nitrite is not particularly limited, and examples thereof include sodium nitrite, potassium nitrite, calcium nitrite, and the like. Especially, sodium nitrite or potassium nitrite is desirable.

The nitrite concentrations of the buffer solutions are not particularly limited as long as the nitrite is dissolved to be used. However, the desirable lower limit is 0.0001 mol/L, and the desirable upper limit is 5 mol/L. A buffer solution containing the nitrite at a concentration of less than 0.0001 mol/L may fail to deliver excellent separation performance. A buffer solution containing the nitrite at a concentration of more than 5 mol/L may cause an increase in the measurement time, or poor separation performance. The more desirable lower limit is 0.001 mol/L, and the more desirable upper limit is 1 mol/L.

The nitrite may be added to all the above-mentioned buffer solutions (A) to (E), or may be added only to some of the buffer solutions. The nitrite is desirably added to at least the buffer solutions (D) or (E).

An electrophoresis apparatus used in the method for measuring hemoglobin using electrophoresis of the present invention is not particularly limited, and examples thereof include a capillary electrophoresis apparatus, a microdevice electrophoresis apparatus, and the like.

FIG. 1 shows an example of a capillary electrophoresis apparatus used in the method for measuring hemoglobin of the present invention. As shown in FIG. 1, the capillary electrophoresis apparatus 11 is provided with an anode reservoir 12, a cathode reservoir 13, a capillary 14, a high-voltage power supply 15, a detector 16, and a pair of electrodes 17 and 18. Each end of the capillary 14 is immersed in a buffer solution in the anode reservoir 12 or the cathode reservoir 13, and the inside of the tubular capillary 14 is filled with the buffer solution. The electrodes 17 and 18 are electrically connected with the high-voltage power supply 15.

In the method for measuring hemoglobin of the present invention, the inner surface the capillary 14 serving as the migration path is coated with a cationic substance to be immobilized thereon, or the capillary 14 is made of a cationic material. The respective buffer solutions in the anode reservoir 12, the cathode reservoir 13, or the capillary 14 desirably contain the water-soluble polymer having an anionic group.

For measurement of hemoglobin, a sample is injected into the capillary 14 from one end, and a predetermined voltage is applied by the high-voltage power supply 15 to measure a target measurement component traveling in the capillary 14 with the detector 16.

The length of the capillary 14 is not particularly limited, and the desirable lower limit thereof is 10 mm, and the desirable upper limit thereof is 800 mm. In the case where the length of the capillary 14 is less than 10 mm, a measurement sample may be insufficiently separated, which in turn may prevent accurate measurement. In the case where the length of the capillary 14 is more than 800 mm, it may take longer to measure, or an obtained electropherogram may have a deformed peak, which in turn may prevent accurate measurement.

The width or the diameter of the capillary 14 is not particularly limited, and the desirable lower limit thereof is 1 μm, and the desirable upper limit thereof is 200 μm. In the case where the width or the diameter of the capillary 14 is less than 1 μm, the optical path length for detection by a detector is short, possibly leading to low measurement accuracy. In the case where the width or the diameter of the capillary 14 is more than 200 μm, an obtained electropherogram may have a broad peak due to diffusion of the sample inside the migration path, possibly leading to low measurement accuracy.

In the method for measuring hemoglobin using electrophoresis of the present invention, a microdevice electrophoresis apparatus is particularly desirably used.

An electrophoresis apparatus used in the method for measuring hemoglobin of the preset invention, which includes: a measurement unit including a microdevice having electrodes, and a migration path having an inner surface coated with a cationic substance to be immobilized on the inner surface or a migration path having an inner surface made of a cationic material; a power supply unit; and a detection unit is also one aspect of the present invention.

FIGS. 2a and 2b show an example of an electrophoresis apparatus of the present invention. FIG. 2a is a top view schematically showing a microdevice electrophoresis apparatus. As shown in FIG. 2a, the microdevice electrophoresis apparatus is provided with a measurement unit 2 having reservoirs 21, electrodes 22 set in the reservoirs and a flow channel including a migration path 23 in which a measurement sample is moved and separated during electrophoresis. The reservoirs 21 serve as liquid reservoirs for holding a buffer solution.

FIG. 2a shows one example of a microdevice electrophoresis apparatus including a cross-shaped flow channel including the migration path 23, four reservoirs 21 set for the ends of the migration path 23, and the electrodes 22 set in the reservoirs 21. Each electrode 22 is connected with a power supply unit 3 that is a high-voltage power supply via a voltage supply cable 31.

FIG. 2b is a transverse cross-sectional view schematically showing the microdevice electrophoresis apparatus. As shown in FIG. 2b, the microdevice electrophoresis apparatus 1 has a detection unit 4. The detection unit 4 has a light source 41 and a light receiving part 42. The light source 41 and the light receiving part 42 are located on the detection unit 4 on the opposite sides with respect to the measurement unit 2. The light source 41 generates a light having a specific wavelength, and irradiates a predetermined portion of the migration path 23 formed in the measurement unit 2 with the light. The light receiving part 42 measures absorbance of a target measurement component separated in the migration path 23.

The electrophoresis apparatus of the present invention includes a measurement unit including the electrodes, and the microdevice having the migration path having the inner surface coated with a cationic substance to be immobilized on the inner surface or the migration path having the inner surface made of a cationic material.

The microdevice used herein is a flat substrate made of an inorganic or organic material with a size of not more than approximately 150 mm square. Specific examples thereof include conventionally known microchips used in the techniques called μ-TAS or Lab-on-a-chip, and the like.

The material of the microdevice is not particularly limited, and any conventionally known material can be used. Desirable examples thereof include glass materials such as borosilicate glass and quartz, silica based materials such as fused silica and polydimethylsiloxane, resin materials such as polyacrylic resins, polystyrenic resins, polylactic acid resins, polycarbonate resins, and olefinic resins. Especially, the glass materials, the silica materials, and the acrylic resins are desirable.

Here, materials that do not absorb light of a specific wavelength described below are desirable.

The lower limit of the length of the migration path of the microdevice is 10 mm, and the upper limit thereof is 100 mm. In the case where the length of the migration path is less than 10 mm, a sample may be insufficiently separated, which in turn may prevent accurate measurement. In the case where the length of the migration path is more than 100 mm, it may take longer to measure, or an obtained electropherogram may have a deformed peak, which in turn may prevent accurate measurement.

The lower limit of the width of the migration path of the microdevice is 10 μm, and the upper limit thereof is 100 μm. In the case where the width of the migration path is less than 10 μm, the optical path length for detection by the detector is short, possibly leading to low measurement accuracy. In the case where the width of the migration path is more than 100 μm, an obtained electropherogram may have a broad peak due to diffusion of the sample inside the migration path, possibly leading to low measurement accuracy.

The shape of the migration path of the microdevice is not particularly limited, and examples thereof include straight line, curve with a certain curvature, spiral, and the like. Especially, a linear migration path is desirable.

The cross-sectional shape of the migration path is not particularly limited, and examples thereof include rectangle, round, and the like.

The microdevice may have a single migration path, or plural migration paths.

Although depending on the method for immobilizing the cationic group and other factors, the microdevice may be used repeatedly, or may be used only once.

The migration path of the microdevice has the inner surface coated with a cationic substance to be immobilized on the inner surface by the method described above or the inner surface made of a cationic material.

For electrophoresis, the migration path is filled with a buffer solution. The buffer solution used to fill the migration path is the buffer solution used in the measurement method described above, that is, the buffer solution containing the water-soluble polymer having an anionic group.

The measurement unit desirably has reservoirs.

The reservoirs are provided at the ends of the migration path, and serve as supply openings and discharge openings of the buffer solution used for electrophoresis, a measurement sample, etc., and electrode inlet ports.

The shape of the reservoir is not particularly limited, and reservoirs having a conventionally known shape can be used. The size of the reservoir is not particularly limited, and reservoirs having a conventionally known size can be used.

In order to supply and discharge the buffer solution, a measurement sample, etc., the reservoir may optionally have a connection part at the bottom or the upper portion to supply and discharge liquid.

The measurement unit has electrodes. The electrode contacts the buffer solution in the flow channel of the measurement unit, and is connected to the power supply unit described below. Voltage supplied from the power supply unit is applied to a measurement sample through the buffer solution filling the flow channel of the measurement unit to allow electrophoresis to run.

The setting positions of the electrodes are not particularly limited as long as the electrodes are set to contact the buffer solution in the flow channel of the measurement unit. The electrodes may be fixed to the measurement unit, or may be fixed to a covering device of the measurement unit, a support base (chip holder) that fixes the measurement unit, or the like. The positions at which the electrodes are allowed to contact the buffer solution are not particularly limited as long as the electrodes are at opposite positions on the flow channel outer from the migration path. However, the electrodes are desirably allowed to contact the buffer solution in the reservoirs.

The material of the electrode is not particularly limited, and a conventionally known material such as a conductive metal like platinum can be used.

The electrophoresis apparatus of the present invention has a power supply unit. The power supply unit functions to supply voltage for electrophoresis.

The desirable lower limit of voltage to be applied by the power supply unit is 100 V, and the desirable upper limit thereof is 3000 V. In the case where a voltage of less than 100 V is applied, a target measurement component may be insufficiently moved by electrophoresis. In the case where a voltage of more than 3000 V is applied, an obtained electropherogram may have problems such as deformed peaks, due to generation of Joule heat, etc., possibly leading to low measurement accuracy.

The power supply unit is connected with the electrodes set in the reservoirs and the like of the measurement unit to supply voltage to the buffer solution in the measurement unit.

The method for connecting the power supply unit and the electrode is not particularly limited, and examples thereof include a method using a conventionally known code and the like.

The electrophoresis apparatus of the present invention has a detection unit.

The detection unit is a mechanism for optically detecting components in a measurement sample separated by electrophoresis. The principle of the optical detection is not particularly limited as long as it allows detection of hemoglobin as a measurement sample. However, an absorption spectroscopy using visible light in the maximum absorption wavelength range of hemoglobin is simple and desirable.

Specifically, the absorbance of visible light can be measured, for example, as follows. A predetermined position of the migration path is irradiated with light including visible light from a light source. The absorbance of visible light of various components of hemoglobin traveling in the inside of the migration path is measured in a light receiving device set on the opposite side across the migration path.

The detection unit is desirably provided with the light source and the light receiving device.

In the detection unit, arrangement of the light source and the light receiving device is not particularly limited, and, for example, the light source and the light receiving device may be set across the migration path on an upper portion and a lower portion of the measurement unit, or may be set across the migration path on side portions of the measurement unit.

In the detection unit, the direction of light emitted from the light resource to the light receiving device may be from above to below, from below to above, or from side to side depending on the arrangement of the light resource and the light receiving device. Alternatively, the light may be emitted with a predetermined angle.

In the electrophoresis apparatus of the present invention, the migration path is pre-filled with the buffer solution. The above-mentioned phrase "pre-filled with the buffer solution" implies that it is possible to avoid the procedure for filling the migration path with the buffer solution to be carried out immediately before performing electrophoresis. Namely, for example, the migration path is filled with the buffer solution, and then left to stand for a certain period of time. This enables electrophoresis to be performed using the buffer solution having been poured to fill the migration path, that is, without pouring the buffer solution to fill the migration path again. The phrase also implies that any substances except a measurement sample are not added to the migration path from start to finish of the measurement.

Conventional microdevice electrophoresis apparatuses require a migration path on a microdevice to be filled with a buffer solution immediately before measurement, and to be set in the electrophoresis apparatus to start the measurement. Alternatively, the microdevice with its migration path not filled with the buffer solution is set for electrophoresis, and then the migration path on the microdevice is filled with the buffer solution immediately before measurement using a filling mechanism provided in the electrophoresis apparatus. Thus, in the conventional electrophoresis apparatuses, preparation of the microdevice with its migration path not filled with the buffer solution is the first step of the measurement.

On the other hand, the electrophoresis apparatus of the present invention does not require filling the migration path with the buffer solution immediately before measurement because the migration path is pre-filled with the buffer solution. Therefore, the electrophoresis apparatus does not need a mechanism such as a buffer solution filling mechanism.

In addition, the migration path can be preserved for a long period of time with the buffer solution filling the migration path. This is because the electrophoresis apparatus of the present invention has the migration path having the inner surface coated with the cationic substance to be immobilized on the inner surface, or the migration path having the inner surface made of the cationic material.

When a migration path having a length of 10 to 100 mm and a width of 10 to 100 μm is used in the electrophoresis apparatus of the present invention, the desirable pH of the buffer solution is 5.0 to 6.0, the desirable buffer composition concentration, that is, the desirable salt concentration of the buffer solution is 10 to 300 mM, and the desirable voltage to be applied for electrophoresis is 100 to 2000 V.

The method for measuring hemoglobin using the electrophoresis apparatus of the present invention in which a microdevice having a migration path with a length of 10 to 100 mm and a width of 10 to 100 μm, and a buffer solution having a pH of 5.0 to 6.0 and a salt concentration of 10 to 300 mM are used, and a voltage of 100 to 2000 V is applied is also one aspect of the present invention.

The buffer solution used in this case contains the water-soluble polymer having an anionic group, and has a pH of 5.0 to 6.0, and a salt concentration of 10 to 300 mM, and the buffer composition can be used at an adjusted pH and an adjusted salt concentration.

In the detection unit of the electrophoresis apparatus of the present invention, one wavelength is selected from a range of from 400 to 430 nm as a dominant wavelength, and one wavelength is selected from a range of from 450 to 600 nm as a subwavelength, and the absorbance at the dominant wavelength and the absorbance at the subwavelength are desirably measured at the same time. Selection of specific wavelengths as described above enables low-cost and high-accuracy measurement in a short time.

The method for measuring hemoglobin using the electrophoresis apparatus of the present invention in which light including a dominant wavelength selected from a range of from 400 to 430 nm and a subwavelength selected from a range of from 450 to 600 nm in the detection unit is also one aspect of the present invention.

The desirable range of the dominant wavelength is 410 to 420 nm, and the desirable range of the sub wavelength is 500 to 550 nm.

In the method for measuring hemoglobin of the present invention, only visible light in a range including the dominant wavelength and visible light in a range including the subwavelength may be emitted to measure the absorbance at the dominant wavelength and the absorbance at the subwavelength. Alternatively, the absorbances at some wavelengths in a range including the dominant wavelength, and the absorbances at some wavelengths in a range including the subwavelength may be measured, only the absorbance at the dominant wavelength and the absorbance at the subwavelength may be selected. In either case, a peak area value of a target hemoglobin can be calculated by producing an electropherogram based on the difference between the absorbance at the dominant wavelength and the absorbance at the subwavelength measured at the same time (the absorbance at the dominant wavelength—the absorbance at the subwavelength).

A method for measuring the absorbance at the dominant wavelength and the absorbance at the subwavelength is not particularly limited, and for example, a conventionally known detection technique such as a wavelength filter, a spectroscope, a mirror of any type or a lens of any type can be used.

Attachment components may be provided in the electrophoresis apparatus of the present invention in addition to the basic components: the measurement unit; the power supply unit; and the detection unit. Such attachment components allow electrophoresis to be more efficiently performed.

The attachment components are not particularly limited, and examples thereof include a control mechanism for controlling voltage applied by the power supply unit, and polarity and application time thereof, and for performing a series of automatization programs; a supply and discharge mechanism for supplying and discharging a cleaning liquid and the like for optionally washing the reservoirs, the migration path and the electrodes; a data-processing mechanism for producing an electropherogram based on the measured absorbance, and calculating and printing stable HbA1c values; an automatic dilution mechanism for automatically diluting a measurement sample, or automatically supplying a measurement sample to the measurement unit; a sample container; a mechanism for washing a dilution reservoir or a flow channel; a mechanism for installing or supplying the sample container; and other mechanisms.

The electrophoresis apparatus of the present invention allows a mechanism for measuring glucose to be installed in the measurement unit. Use of this measurement unit enables simultaneous measurement of two substances, that is, glucose and stable HbA1c, which is used as an indicator of diabetes diagnosis.

The mechanism for measuring glucose is not particularly limited, and any conventionally known measurement mechanism can be used. Examples thereof include a mechanism using a reduction method in which a reductive effect of glucose in an alkaline solution is utilized; a mechanism using a condensation method in which the condensation reaction of glucose and an aromatic amine is utilized; a mechanism using an enzyme method in which a reaction of glucose and an enzyme such as glucose dehydrogenase, glucose oxidase, and hexokinase is utilized; and other mechanisms. Especially, the mechanism using an enzyme method is desirable.

The mechanism for measuring glucose is desirably provided on the microdevice that is the measurement unit of the electrophoresis apparatus.

When the measurement mechanism of glucose, for example, the mechanism using an enzyme method, is formed into a part of the microdevice, a known method such as a method in which platinum thin film electrodes or the like are formed on the microdevice by a process such as sputtering, and glucose dehydrogenase, glucose oxidase, or the like is immobilized on these electrodes to form an enzyme sensor on the microdevice can be used.

The hemoglobin measurement mechanism by electrophoresis and glucose measurement mechanism by electrophoresis may be formed on different microdevices, or may be formed on the same microchip.

When both mechanisms are formed on the same microdevice, an independent flow channel may be provided for each measurement, or a mechanism capable of both measurements using the same flow channel may be provided. FIGS. 3a to 3c show specific examples of structures.

FIG. 3a shows an example of a structure in which a sample supply opening for hemoglobin measurement (reference numeral 26 in the figure) and a sample supply opening for glucose measurement (reference numeral 27 in the figure) are independently provided. In this structure, hemoglobin is measured as follows: introducing a sample into a sample supply opening 26; applying voltage to electrodes 22 to start electrophoresis; separating each component in the migration path 23; and optically detecting each component at a detection position 25. Glucose is measured by separately introducing a sample into a sample supply opening 27 using enzymatic electrodes 28.

In the example of the structure shown in FIG. 3b, one sample is introduced into a sample supply opening 29, the sample is led to a reservoir 211 for hemoglobin measurement and a reservoir 212 for glucose measurement, and then voltage is applied between the reservoir 211 and a reservoir 21 to allow electrophoresis of hemoglobin to be performed in a migration path 23. Glucose is measured by enzymatic electrodes 28 in the reservoir 212.

In the example of the structure shown in FIG. 3c, a sample is introduced into a sample supply opening 29, and glucose is measured first by enzymatic electrodes 28 in the opening 29. Thereafter, voltage is applied to electrodes set in the opening 29 and a reservoir 21 to allow electrophoresis to be performed in a migration path 23 for separation of hemoglobin.

All of the above-mentioned structures have the components of the above-mentioned electrophoresis apparatus of hemoglobin, and additionally have a known component for glucose measurement on the measurement unit of the apparatus. Any structure can be adapted as long as it includes the essential components, that is, the above-mentioned basic components. Structures other than those shown in FIG. 3 are also within the scope of the present invention.

A method for simultaneously measuring hemoglobin and glucose in which an electrophoresis apparatus of this type is used to make it possible to measure both of hemoglobin and glucose in the single apparatus is also within the scope of the present invention.

A measurement system using independent mechanisms similar to those shown in FIG. 3a, or a measurement system using linked mechanisms similar to that shown in FIG. 3b or 3c may be used to measure hemoglobin and glucose by the above-mentioned method using electrophoresis. The independent mechanisms enable measurement of only one target, that is, either of hemoglobin or glucose without allowing the mechanism for measuring the non-target to run, leading to cut down of reagent consumption, and the like. On the other hand, the linked mechanisms enable simultaneous measurement of both by introducing one measurement sample. The linked mechanisms also enable measurement of only either one, needless to say.

Hemoglobin and glucose may be measured in any order, as described in, for example, the description of the mechanisms of FIG. 3c. One target may be measured followed by another one, or both may be simultaneously measured.

An apparatus of this type can be assembled at a low cost, and use of this apparatus enables simultaneous or separate measurement of hemoglobin and glucose with high accuracy in a short time in the one apparatus.

Hemoglobin to be measured in the method for measuring hemoglobin of the present invention or by the electrophoresis apparatus of the present invention is not particularly limited. Examples thereof include conventionally known hemoglobins. Specific examples include HbA1a, HbA1b, HbF, unstable HbA1c, stable HbA1c, HbAo and HbA2; modified Hbs such as acetylated Hbs and carbamylated Hbs; and abnormal Hbs such as HbS and HbC; and other hemoglobins. Especially, stable HbA1c can be suitably measured.

Use of the method for measuring hemoglobin and the electrophoresis apparatus enables simultaneous separation of stable hemoglobin A1c and abnormal hemoglobins. The method for simultaneously measuring stable hemoglobin A1c and abnormal hemoglobins by the method for measuring hemoglobin and the electrophoresis apparatus is also one aspect of the present invention.

For clinical diagnosis of diabetes mellitus, stable HbA1c, which is a type of HbA1c and used as a diabetic indicator, should be separated from unstable HbA1c, fetal hemoglobin, modified Hbs such as carbamylated Hbs and abnormal hemoglobins such as HbS. According to the method for measuring hemoglobin of the present invention, it is possible to obtain an electropherogram having a stable hemoglobin A1c peak separated from peaks of other hemoglobins. Use of such an electropherogram enables more accurate and stable measurement of stable hemoglobin A1c compared to conventional techniques.

In conventional methods for measuring stable hemoglobin A1c, a stable HbA1c value is calculated by determining a ratio of a peak area value of stable HbA1c to a peak area value of all Hbs. However, stable HbA1c values calculated as described above in each measurement show large variations when a sample containing abnormal Hbs is measured. Therefore, there has been a problem that the stable HbA1c value cannot be accurately calculated.

The present inventors conducted intensive studies to find out that the reason why the stable HbA1c values show large variation when the stable HbA1c value is measured by electrophoresis in conventional techniques, particularly for a sample containing abnormal Hbs, is that unnecessary peak area values in an obtained electropherogram are also involved in calculation of the stable HbA1c value.

Therefore, the present inventors found out two methods: a method in which the stable HbA1c value is calculated without using peak area values unnecessary for calculation of the stable HbA1c value in an obtained electropherogram (first calculation method); and a method in which the stable HbA1c value is calculated using only selected peak area values necessary for calculation of the stable HbA1c value (second calculation method). Techniques that make it possible to provide an electropherogram having a stable hemoglobin A1c peak separated from other hemoglobin peaks enable calculation by these calculation methods.

The first step of the first calculation method is to obtain an electropherogram having a stable hemoglobin A1c peak separated from peaks of abnormal hemoglobins and a fetal hemoglobin peak by the method using electrophoresis of the present invention or the electrophoresis apparatus of the present invention. The stable HbA1c peak area value a of the obtained electropherogram is calculated. Subsequently, an all-Hb peak area value d, an all-abnormal-Hb peak area value, and a fetal-hemoglobin peak area value are calculated. Secondly, a peak area value b is calculated by subtraction of the all-abnormal-Hb peak area value and the fetal-hemoglobin peak area value from the all-Hb peak area value d. A stable HbA1c value (%) can be obtained by multiplying by 100 a value determined by dividing the obtained area value a by the area value b, that is, by the following formula (1).

A method for calculating the peak area values of each Hb is not particularly limited, and examples thereof include conventionally known data processing methods, and other methods.

[Formula 1]

$$\text{Stable Hemoglobin } A1c \text{ value} = \frac{\text{Peak Area Value } a}{\text{Peak Area Value } b} \times 100(\%) \quad (1)$$

The first step of the second calculation method is to obtain an electropherogram having a stable hemoglobin A1c peak separated from a hemoglobin $A_0$ peak by the method using electrophoresis of the present invention or the electrophoresis apparatus of the present invention. The stable HbA1c peak area value a of the obtained electropherogram is calculated. Subsequently, a hemoglobin $A_0$ peak area value c is calculated. A stable HbA1c value (%) can be obtained by multiplying by 100 a value determined by dividing the obtained area value a by the sum of the area value a and the area value c, that is, by the following formula (2).

A method for calculating the peak area values of each Hb is not particularly limited, and examples thereof include conventionally known data processing methods, and other methods.

[Formula 2]

$$\text{Stable Hemoglobin } A1c \text{ value} = \frac{\text{Peak Area Value } a}{\text{Peak Area Value } a + \text{Peak Area Value } c} \times 100(\%) \quad (2)$$

These methods for calculating the stable hemoglobin A1c value enable accurate calculation of the stable HbA1c value, which is used as a diabetic indicator, using a sample containing abnormal Hbs and the like. Examples of a method for producing an electropherogram having a stable hemoglobin A1c peak separated from peaks of abnormal hemoglobins and a fetal hemoglobin peak used in the first calculation method, and a method for producing an electropherogram having a stable hemoglobin A1c peak separated from a hemoglobin $A_0$ peak used in the second calculation method include the method for measuring hemoglobin of the present invention.

EFFECTS OF THE INVENTION

The present invention can provide a method for measuring hemoglobin that enables short-time, high-accuracy measurement of hemoglobin, in particular stable hemoglobin A1c, which is used as a diagnostic indicator of diabetes mellitus, and an electrophoresis apparatus that is suitably used in this measurement method.

BEST MODE FOR CARRYING OUT THE INVENTION

Hereinafter, the aspects of the present invention will be described in detail by way of examples. However, the present invention is not limited only to these examples.

Example 1

A migration path with a cationic polymer immobilized thereon was used, and a buffer solution containing a water-soluble acrylic polymer having an anionic group was used as the electrophoresis buffer solution for measurement in each of Examples 1 to 3.

(1) Coating of Migration Path

A 0.2N hydrochloric acid solution containing 0.2% by weight of chitosan (chitosan 100, produced by Wako Pure Chemical Industries, Ltd.) as the cationic polymer was prepared. Next, a 0.2N NaOH aqueous solution, ion exchange water, and a 0.5N HCl aqueous solution were allowed to flow through a capillary made of fused silica (produced by GL Sciences, Inc., 25 μm in inside diameter×30 cm in full length) in this order to wash the inside of the capillary, and then the prepared chitosan solution was allowed to flow through the capillary for 20 minutes. Subsequently, air was injected into the capillary to send out the chitosan solution, and then the capillary was dried in a drier at a temperature of 40° C. for 12 hours. Thereafter, the chitosan solution was injected again, and the procedure of injection of air and drying was repeated 5 times. Thus, the inner surface of the capillary was coated.

The prepared capillary having the inner surface coated with chitosan (cationic polymer) was set in a capillary electrophoresis apparatus (PAC/E MDQ, produced by Beckman Coulter, Inc.).

(2) Preparation of Buffer Solution

An amount of 3.0 g of 2-acrylamide-2-methylpropanesulfonic acid (produced by Wako Pure Chemical Industries, Ltd.) as the acrylic monomer having an anionic group, and 2.0 g of hydroxyethyl methacrylate (produced by Wako Pure Chemical Industries, Ltd.) as the acrylic monomer without anionic groups were dissolved in 50 mL of ion exchange water. To the obtained solution was added 0.05 g of potassium persulfate, and the solution was heated to 80° C. under stirring in a nitrogen atmosphere to allow polymerization to proceed. The whole mixture obtained by 10-hour polymerization was poured into a dialysis tube (produced by Sanko Junyaku Co., Ltd., UC C65-50), and dialyzed in ion exchange water for 12 hours to obtain an acrylic polymer to be used as the buffer solution. A citrate buffer solution (pH 4.7) containing 2.0% by weight of the obtained acrylic polymer was set to each end of the capillary to fill the capillary with the buffer solution.

(3) Measurement of Healthy Human Blood

A blood sample was collected from a healthy human with heparin. To 70 μL of this healthy human whole blood sample was added 200 μL of a citrate buffer solution (pH 6.0) containing 2% by weight of the acrylic polymer prepared in the process (2) to hemolyze and dilute the blood sample. The sample thus obtained was used as a measurement sample.

The sample was injected into the capillary from one end, and subjected to electrophoresis by applying a voltage of 20 kV to the buffer solutions set for the ends of the capillary to measure transition of visible light absorbance at 415 nm. Thus, stable HbA1c in the human blood was measured by capillary electrophoresis.

FIG. 4 is an electropherogram obtained by the measurement of the healthy human blood sample in Example 1. In FIG. 4, the peak 1 represents stable HbA1c, and the peak 2 represents HbAo. The results show that stable HbA1c could be separated.

(4) Measurement of Sample Containing Modified Hb

To a healthy human whole blood sample collected from a healthy human with heparin was added glucose to give a concentration of 2000 mg/dL. Thus, a sample containing a large amount of unstable HbA1c that is a form of modified Hbs was artificially prepared.

The sample was injected into the capillary from one end, and subjected to electrophoresis by applying a voltage of 20 kV to the buffer solutions set for the ends of the capillary to measure transition of visible light absorbance at 415 nm. Thus, stable HbA1c in the human blood was measured by capillary electrophoresis.

FIG. 5 is an electropherogram obtained by the measurement of the sample containing the modified Hb in Example 1.

In FIG. 5, the peak 1 represents stable HbA1c, the peak 2 represents HbAo, and the peak 3 represents the modified Hb (unstable HbA1c). As shown in FIG. 5, stable HbA1c and unstable HbA1c that is a form of modified Hbs were favorably separated.

(5) Separation Performance Test of Modified Hb

Glucose was added to the healthy human blood sample to give a concentration of 2000 mg/dL to prepare a sample containing unstable HbA1c as described in the process (4). Sodium cyanate was added to a healthy human blood sample collected from the same person to give a concentration of 50 mg/dL. Thus, a sample containing a carbamylated Hb was prepared. Both samples together with the healthy human blood sample were measured under the above-mentioned conditions.

An electropherogram obtained by the measurement of the sample containing the carbamylated Hb was similar to the electropherogram shown in FIG. 5. Accordingly, the results show that stable HbA1c were favorably separated.

Table 1 shows values (ΔHbA1c value) calculated by subtraction of the stable HbA1c value of the healthy human blood sample from the stable HbA1c values of each of the samples containing the modified Hb.

(6) Within-Run Reproducibility Test

One healthy human blood sample was continuously measured 10 times under the conditions of Example 1, and a CV value of the stable HbA1c values determined by the measurement was calculated.

The CV value was determined by dividing the standard deviation by the average value (standard deviation/average value). Table 2 shows the results.

Example 2

The inner surface of the capillary was coated by the same method as in Example 1, except that 0.5% by weight aqueous solution of polybrene (produced by Nacalai Tesque, Inc.) as the cationic polymer was used instead of the chitosan solution. The healthy human blood sample prepared in the process (3) of Example 1 and the sample containing the modified Hb prepared in the process (4) of Example 1 were measured using the same buffer solution containing the acrylic polymer as that used in Example 1. An electropherogram obtained by the measurement of the healthy human blood sample was similar to that shown in FIG. 4. An electropherogram obtained by the measurement of the sample containing the modified Hb was similar to that shown in FIG. 5.

The modified Hb separation performance test and the within-run reproducibility test were performed by the same methods as in the processes (5) and (6) of Example 1, respectively. Table 1 and 2 show the respective results.

Example 3

In Example 3, a migration path with a cationic polymer immobilized thereon was used, and a buffer solution containing a water-soluble acrylic polymer having an anionic group was used as the electrophoresis buffer solution, like in Examples 1 and 2. In addition, a microdevice type electrophoresis apparatus including a measurement unit, a power supply unit, and a detection unit was assembled for measurement.

A microdevice electrophoresis apparatus shown in FIG. 2 was assembled. A glass microdevice (outside dimensions: 50 mm×75 mm×3 mm) including platinum electrodes (1 mm in diameter×5 mm in length) and a cross-shaped migration path (length: 50 mm, width: 80 µm) was used as the measurement unit. The electrophoresis apparatus was assembled as follows: inserting the electrodes into reservoirs on the microdevice; connecting the electrodes and the power supply unit (produced by LabSmith, multi-channel high-voltage sequencer electric power supply device, HVS448) via a voltage supply code; and setting the detection unit including a halogen lamp light source (produced by Moritex Corp., MHF-V501), a spectroscope (produced by B&W Tek, Inc., BTC112), and a computer for data processing on the microdevice.

The migration path of the microdevice was coated by the same method as in Example 1, except that a 0.2N hydrochloric acid solution containing 0.2% by weight of chitosan (chitosan 100, produced by Wako Pure Chemical Industries, Ltd.) was used. The healthy human blood sample and the sample containing the modified Hb were measured using the same buffer solution containing the acrylic polymer as that used in Example 1 by microdevice electrophoresis at a voltage of 1000 V.

FIG. 6 is an electropherogram obtained in Example 3 by the measurement of the healthy human blood sample prepared in the process (3) of Example 1. In FIG. 6, the peak 1 represents stable HbA1c, and the peak 2 represents HbAo. FIG. 7 is an electropherogram obtained in Example 3 by the measurement of the sample containing the modified Hb prepared in the process (4) of Example 1. In FIG. 7, the peak 1 represents stable HbA1c, the peak 2 represents HbAo, and the peak 3 represents the modified Hb (unstable HbA1c). As shown in FIG. 7, stable HbA1c and unstable HbA1c that is a form of modified Hbs were favorably separated. The modified Hb separation performance test and the within-run reproducibility test were performed by the same methods as in the processes (5) and (6) of Example 1, respectively. Table 1 and Table 2 show the respective results.

Comparative Example 1

A migration path with a cationic polymer immobilized thereon was used like in Examples 1 and 2, but a buffer solution without the water-soluble acrylic polymer having an anionic group was used for measurement in Comparative Example 1.

The healthy human blood sample prepared in the process (3) of Example 1 and the sample containing the modified Hb prepared in the process (4) of Example 1 were measured by the same method as in Example 1 except that a citrate buffer solution (pH 4.7) without acrylic polymers was used instead of the citrate buffer solution containing the acrylic polymer (prepared in Example 1). No peak was detected in electropherograms obtained by the measurement of both samples. Thus, the results show that hemoglobins could not be separated when using a buffer solution without the water-soluble polymer having an anionic group.

Comparative Example 2

A cationic polymer was used for coating like in Examples 1 and 2, but a dynamic coating technique was used as the coating method instead of the immobilized coating method in Comparative Example 2. A buffer solution containing a water-soluble non-acrylic polymer having an anionic group was used as the buffer solution for measurement.

In order to wash the inside of a capillary made of fused silica (produced by GL Sciences, Inc., 25 µm in inside diameter×30 cm in full length), a 0.2N NaOH aqueous solution, ion exchange water, and a 0.5N HCl aqueous solution were allowed to flow through the capillary in this order. A malate buffer solution (pH 4.7) containing 0.5% by weight of horse serum albumin (cationic polymer) was allowed to flow through the capillary for 1 minute to dynamically coat the inside of the capillary with the buffer solution. Next, a malate buffer solution (pH 4.7) containing 0.2% by weight of chondroitin sulfate (produced by Wako Pure Chemical Industries, Ltd., non-acrylic polymer) was set for each end of the capillary to fill the capillary with the buffer solution.

The sample containing the modified Hb prepared in the process (4) of Example 1 was measured by the same method as in Example 1.

FIG. 8 is an electropherogram obtained by the measurement of the sample containing the modified Hb in Comparative Example 2.

In FIG. 8, the peak 1 represents stable HbA1c, the peak 2 represents HbAo, and the peak 3 represents the modified Hb (unstable HbA1c). As shown in FIG. 8, the peak 1 representing stable HbA1c overlaps the peak 3 representing the modified Hb in the obtained electropherogram. The results show that stable HbA1c cannot be separated from the modified Hb and accurately measured when the dynamic coating technique is used instead of the immobilized coating method of the present invention, and the buffer solution without the acrylic polymers was used.

The modified Hb separation performance test and the within-run reproducibility test were performed by the same methods as in the processes (5) and (6) of Example 1, respectively. Here, in the within-run reproducibility test in Comparative Example 2, 0.2N NaOH and a malate buffer solution (pH 4.7) containing 0.2% by weight of chondroitin sulfate were sequentially allowed to flow through the capillary for 1 minute and 2 minutes, respectively, after each measurement to wash the capillary. In addition, the dynamic coating technique described in Comparative Example 2 was performed again for repetitive measurement. Thus, the within-run reproducibility test was performed.

Table 1 and Table 2 show the respective results.

TABLE 1

| | ΔHbA1c value (%) (Sample containing modified Hb - Healthy human sample) | |
| --- | --- | --- |
| | Sample containing unstable HbA1c | Sample containing carbamylated Hb |
| Example 1 | 0.0 | 0.1 |
| Example 2 | −0.1 | 0.1 |
| Example 3 | 0.1 | 0.2 |
| Comparative Example 2 | 0.4 | −1.3 |

Table 1 shows that the ΔHbA1c value obtained under the measurement conditions of Example 1 was remarkably small, that is, only a slight difference is found in the stable HbA1c values of the sample containing the modified Hb and the healthy human blood sample without the modified Hb. Accordingly, the results show that stable HbA1c can be accurately measured under the measurement conditions of Example 1 even under the presence of modified Hbs. The results of Examples 2 and 3 were also favorable like in Example 1. However, the ΔHbA1c value obtained under the measurement conditions of Comparative Example 2 was large. Accordingly, the results show that the measurement under the conditions of Comparative Example 2 is not accurate.

TABLE 2

| | Within-run reproducibility test CV (%) |
| --- | --- |
| Example 1 | 0.93 |
| Example 2 | 1.00 |
| Example 3 | 1.05 |
| Comparative Example 2 | 3.36 |

As shown in Table 2, the CV value indicating the data variation obtained by the within-run reproducibility test under the measurement conditions of Example 1 was as good as about 1%. The results of Examples 2 and 3 were also favorable like in Example 1. On the contrary, the CV value obtained by the measurement conditions of Comparative Example 2 was remarkably large and completely unsatisfactory for use in control of the HbA1c value of diabetics.

Example 4

A migration path with a hydrophilic compound having a molecular weight of 200 to 800 with a cationic group linked to the migration path by a covalent bond was used, and a buffer solution containing a water-soluble polymer having an anionic group was used as the electrophoresis buffer solution for measurement in each of Examples 4 to 6.

(1) Preparation of Migration Path

A capillary made of fused silica (produced by GL Sciences, Inc., 25 μm in inside diameter×30 cm in full length) was set in a capillary electrophoresis apparatus (produced by Beckman Coulter, Inc., PAC/E MDQ). In order to wash the inside of the capillary, a 0.2N NaOH solution, ion exchange water, and a 0.5N HCl solution were allowed to flow through the capillary in this order. Thereafter, an aqueous solution containing 1.0% by weight of 3-aminopropyltriethoxysilane (hydrophilic compound, molecular weight: 221, produced by Shin-Etsu Silicones) was allowed to flow through the capillary for 60 minutes. Subsequently, air was injected into the capillary to send out the aqueous solution, and then the capillary was dried in a drier at a temperature of 40° C. for 12 hours. Thus, the capillary having the hydrophilic compound linked by a covalent bond to form the innermost surface of the capillary was prepared.

(2) Preparation of Measurement Sample

A blood sample was collected from a healthy human with EDTA. To 70 μL of this healthy human whole blood sample was added 200 μL of a citrate buffer solution (pH 6.0) containing 0.01% by weight of Triton X-100 (produced by Wako Pure Chemical Industries, Ltd.) to hemolyze and dilute the blood sample. The sample thus obtained was used as a healthy human blood sample.

To 70 μL of a healthy human whole blood sample collected from the same healthy person with EDTA was added glucose to give a concentration of 2500 mg/dL, and warmed at a temperature of 37° C. for 3 hours to artificially prepare a sample containing a large amount of unstable HbA1c that is a form of modified Hb. The sample thus prepared was used as a sample containing the modified Hb.

(3) Measurement by Electrophoresis

The healthy human blood sample and the sample containing the modified Hb were measured using the capillary having the surface linked with the hydrophilic compound by a covalent bond. A 240 mM citrate buffer solution (pH 5.0) containing 2.0% by weight of chondroitin sulfate (anionic polymer, produced by Wako Pure Chemical Industries, Ltd.) was used as the electrophoresis buffer solution. The healthy human sample or the sample containing the modified Hb was injected into the capillary from one end, and subjected to electrophoresis at a voltage of 20 kV to measure absorbance at 415 nm.

The electropherogram obtained by the measurement of the healthy human blood sample in Example 4 was similar to that shown in FIG. 4. The stable HbA1c peak was favorably separated.

The electropherogram obtained by the measurement of the sample containing the modified Hb in Example 4 was similar to that shown in FIG. 5. Stable HbA1c was favorably separated from unstable HbA1c that is a form of modified Hbs.

The modified Hb separation performance test and the within-run reproducibility test were performed using the samples prepared in the process (2) by the same methods as in the processes (5) and (6) of Example 1, respectively. Table 3 and Table 4 show the respective results.

Example 5

(1) Preparation of Migration Path

A migration path with a hydrophilic compound having a molecular weight of 200 to 800 with a cationic group linked to the migration path by a covalent bond was used, and a buffer solution containing a water-soluble polymer having an anionic group was used as the electrophoresis buffer solution in Example 5 like in Example 4. In addition, a microdevice type electrophoresis apparatus including a measurement unit, a power supply unit and a detection unit similar to that of Example 3 was assembled for measurement.

A double-T-shaped electrophoresis flow channel having a width of 90 μm was formed on a microdevice made of polydimethylsiloxane (outside dimensions: 50 mm×75 mm×3 mm). A 0.1N NaOH solution, ion exchange water, and a 0.2N HCl solution were allowed to flow through the formed flow channel in this order to wash the inside of the flow channel. Thereafter, an aqueous solution containing 1.0% by weight of 3-aminopropyltrimethoxysilane (hydrophilic compound, molecular weight: 179, produced by Shin-Etsu Silicones) was allowed to flow through the flow channel for 30 minutes. Subsequently, air was injected into the flow channel to send out the aqueous solution, and then the capillary was dried in a drier at a temperature of 40° C. for 12 hours. Thus, the flow channel having the hydrophilic compound linked by a covalent bond to form the innermost surface of the flow channel was prepared.

(2) Measurement Sample

A healthy human blood sample and a sample containing the modified Hb were prepared by the same method as in Example 4.

(3) Measurement by Electrophoresis

The healthy human sample and the sample containing the modified Hb were measured using the flow channel having the hydrophilic compound linked to the surface by a covalent bond. A 250 mM succinate buffer solution (pH 5.2) containing 2.0% by weight of chondroitin sulfate (anionic polymer, produced by Wako Pure Chemical Industries, Ltd.) was used as the electrophoresis buffer solution. The healthy human sample or the sample containing the modified Hb was injected into the flow channel from one end, and subjected to electrophoresis at a voltage of 0.8 kV to measure absorbance at 415 nm.

The electropherogram obtained by the measurement of the healthy human blood sample was similar to that shown in FIG. 6. The electropherogram obtained by the measurement of the sample containing the modified Hb was similar to that shown in FIG. 7.

The modified Hb separation performance test and the within-run reproducibility test were performed using the measurement samples prepared in the process (2) by the same methods as in the processes (5) and (6) of Example 1, respectively. Table 3 and Table 4 show the respective results.

Example 6

(1) Preparation of Migration Path

A double-T-shaped electrophoresis flow channel having a width of 80 μm was formed on a microdevice made of a copolymer of methyl methacrylate and glycidyl methacrylate (outside dimensions: 50 mm×75 mm×3 mm). A 0.01N NaOH solution, ion exchange water, and a 0.01N HCl solution was allowed to flow through the formed flow channel in this order to wash the inside of the flow channel, and then a 20% by weight aqueous solution of ethylenediamine (hydrophilic compound, molecular weight: 60, produced by Wako Pure Chemical Industries, Ltd.) was allowed to flow through the flow channel for 5 minutes. The both ends of the flow channel filled with this solution were sealed, and the flow channel was left to stand in a constant temperature bath at 50° C. for 3 hours. Subsequently, the inside of the flow channel was washed by the ion exchange water. A 0.05N sulfuric acid was allowed to flow through the flow channel for 3 minutes. The both ends of the migration path filled with this solution were sealed, and the migration path was left to stand in a constant temperature bath at 50° C. for 5 hours. Thereafter, the inside of the flow channel was washed by the ion exchange water. Thus, the flow channel having the hydrophilic compound linked by a covalent bond to form the innermost surface of the flow channel was prepared.

(2) Preparation of Measurement Sample

A healthy human blood sample and a sample containing the modified Hb were prepared by the same method as in Example 4.

(3) Measurement by Electrophoresis

The healthy human sample and the sample containing the modified Hb were measured using the flow channel having the surface linked with the hydrophilic compound by a covalent bond. A 300 mM malate buffer solution (pH 5.2) containing 1.7% by weight of a copolymer including 2-acrylamide-2-methylpropanesulfonic acid (produced by TOAGOSEI Co., Ltd.) was used as the electrophoresis buffer solution. The healthy human sample or the sample containing the modified Hb was injected into the flow channel from one end, and subjected to electrophoresis at a voltage of 1.0 kV to measure absorbance at 415 nm.

The electropherogram obtained by the measurement of the healthy human blood sample was similar to that shown in FIG. 6. The electropherogram obtained by the measurement of the sample containing the modified Hb was similar to that shown in FIG. 7.

The modified Hb separation performance test and the within-run reproducibility test were performed using the measurement samples prepared in the process (2) by the same methods as in the processes (5) and (6) of Example 1, respectively. Table 3 and Table 4 show the respective results.

Comparative Example 3

A migration path with a hydrophilic compound having a cationic group linked thereto by a covalent bond was used for measurement of Comparative Example 3. However, the hydrophilic compound had a larger molecular weight than that of the hydrophilic compound used in the present invention (molecular weight: 200 to 800). A buffer solution containing a water-soluble polymer having an anionic group was used as the electrophoresis buffer solution for measurement.

(1) Preparation of Migration Path

A flow channel with the hydrophilic compound linked by a covalent bond to form the innermost surface of the flow channel was prepared by following the same procedure as in Example 6, except that 0.1% by weight of polylysine (molecular weight: 1000 to 4000, produced by Wako Pure Chemical Industries, Ltd.) was used as the hydrophilic compound.

(2) Preparation of Measurement Sample

The sample containing the modified Hb described in Example 4 was used.

(3) Measurement by Electrophoresis

The sample containing the modified Hb was measured under the same conditions as those of Example 6. Each peak in the obtained electropherogram was favorably separated from the others like in FIG. 7.

The modified Hb separation performance test and the within-run reproducibility test were performed using the measurement samples prepared in the process (2) by the same method as in the processes (5) and (6) of Example 1, respectively. Table 3 and Table 4 show the respective results.

TABLE 3

| | ΔHbA1c value (%) (Sample containing modified Hb - Healthy human sample) | |
|---|---|---|
| | Sample containing unstable HbA1c | Sample containing carbamylated Hb |
| Example 4 | 0.1 | −0.1 |
| Example 5 | 0.0 | −0.1 |
| Example 6 | −0.1 | 0.1 |
| Comaprative Example 3 | −0.2 | 0.3 |

Table 3 shows that the ΔHbA1c values obtained under the respective measurement conditions of Examples 4 to 6 were remarkably small. Accordingly, the results show that stable HbA1c can be accurately measured under the conditions of Examples 4 to 6 even under the presence of modified Hbs. However, the ΔHbA1c value obtained under the measurement conditions of Comparative Example 3 was slightly larger than those obtained in Examples 4 to 6. Accordingly, the results show that measurement under the conditions of Comparative Example 3 was susceptible to modified Hbs.

TABLE 4

| | Within-run reproducibility test CV (%) |
|---|---|
| Example 4 | 1.06 |
| Example 5 | 1.08 |
| Example 6 | 0.99 |
| Comparative Example 3 | 4.22 |

As shown in Table 4, the CV values indicating the data variation obtained by the within-run reproducibility test under the respective measurement conditions of Examples 4 to 6 were as good as about 1%. On the contrary, the CV value indicating the data variation obtained under the measurement conditions of Comparative Example 3 was over 4% which is remarkably large and completely unsatisfactory for use in control of the HbA1c value of diabetics.

Example 7

A migration path coated with a cationic polymer immobilized on an immobilized coating layer of a non-ionic hydrophilic polymer was used, and a buffer solution containing a water-soluble polymer having an anionic group was used as the electrophoresis buffer solution for measurement in each of Examples 7 to 9.

(1) Coating of Inner Surface of Migration Path

A capillary made of fused silica (produced by GL Sciences, Inc., 75 μm in inside diameter×50 cm in full length) was set in a capillary electrophoresis apparatus (produced by Beckman Coulter, Inc., PAC/E MDQ). In order to wash the inside of the capillary, 0.2N NaOH, ion exchange water, and 0.5N HCl were allowed to flow through the capillary in this order. Thereafter, a 1.0% by weight aqueous solution of polyvinyl alcohol (produced by Nihon Synthetic Chemical Industry Co. Ltd., GOHSENOL GH-20, non-ionic hydrophilic polymer) was allowed to flow through the capillary for 20 minutes. Subsequently, air was injected into the capillary to send out the polyvinyl alcohol aqueous solution, and then the capillary was dried in a drier at a temperature of 40° C. for 12 hours. Thereafter, the procedure of injection of the polyvinyl alcohol aqueous solution, injection of air and drying was repeated 5 times to coat the inner surface of the capillary with the non-ionic hydrophilic polymer.

Next, the procedure of injection of the solution, injection of air and drying was repeated 5 times by the same method as that described above to further coat the inner surface of the capillary with an ionic polymer, except that a 5.0% by weight solution of polybrene (produced by Wako Pure Chemical Industries, Ltd., ionic hydrophilic polymer) was used instead of the 1.0% by weight polyvinyl alcohol aqueous solution used in the above process.

(2) Preparation of Measurement Sample

A blood sample was collected from a healthy human with heparin. To 70 μL of this healthy human whole blood sample was added 200 μL of a citrate buffer solution (pH 6.0) containing 0.01% by weight of Triton X-100 (produced by Wako Pure Chemical Industries, Ltd.) to hemolyze and dilute the blood sample. The sample thus obtained was used as a healthy human blood sample.

To 70 μL of a healthy human whole blood sample collected from a healthy human with heparin was added glucose to give a concentration of 2500 mg/dL, and warmed at a temperature of 37° C. for 3 hours to artificially prepare a sample containing a large amount of unstable HbA1c that is a form of modified Hbs. The sample thus prepared was used as the sample containing the modified Hb.

(3) Measurement by Electrophoresis

The healthy human blood sample and the sample containing the modified Hb thus prepared were measured using the above-mentioned capillary. A 200 mM citrate buffer solution (pH 5.0) containing 2.0% by weight of chondroitin sulfate (produced by Wako Pure Chemical Industries, Ltd., water-soluble polymer having an anionic group) was used as the electrophoresis buffer solution. Either of the samples was injected into the capillary from one end, and subjected to electrophoresis at a voltage of 22 kV to measure absorbance at 415 nm.

Each peak in the electropherogram under the measurement conditions of Example 7 was favorably separated from the others like in FIGS. 4 and 5.

The modified Hb separation performance test and the within-run reproducibility test were performed using the measurement samples prepared in the process (2) by the same methods as in the processes (5) and (6) of Example 1, respectively. Table 5 and Table 6 show the respective results.

Example 8

(1) Coating of Inner Surface of Migration Path

A double-T-shaped electrophoresis migration path having a width of 100 μm was formed on a microdevice made of fused silica (7 cm×5 cm). In order to wash the inside of the migration path in the microdevice, 0.1N NaOH, ion exchange water, and 0.2N HCl were allowed to flow through the migration path in this order. A 1.0% by weight aqueous solution of polyvinylpyrrolidone (produced by NIPPON SHOKUBAI Co., Ltd., PVP-K-90W, non-ionic hydrophilic polymer) was allowed to flow through the migration path for 20 minutes. Subsequently, air was injected into the migration path to send out the polyvinylpyrrolidone aqueous solution, and then the migration path was dried in a drier at a temperature of 40° C. for 12 hours. Thereafter, the procedure of injection of the polyvinylpyrrolidone aqueous solution, injection of air and drying was repeated 5 times to coat the inner surface of the migration path with the non-ionic hydrophilic polymer.

Next, the procedure of solution flow through, injection of air and drying was repeated 5 times by the same method as that described above to further coat the inner surface of the migration path with a cationic polymer, except that 0.2N hydrochloric acid containing 2.0% by weight of chitosan (produced by Wako Pure Chemical Industries, Ltd., cationic hydrophilic polymer) was used instead of the 1.0% by weight polyvinylpyrrolidone aqueous solution.

(2) Preparation of Measurement Sample

A healthy human blood sample and a sample containing the modified Hb were prepared by the same method as in Example 7.

(3) Measurement by Electrophoresis

The healthy human sample and the sample containing the modified Hb thus prepared were measured using the above-mentioned migration path. A 250 mM succinate buffer solution (pH 5.2) containing 1.5% by weight of dextran sulfate (produced by Wako Pure Chemical Industries, Ltd., water-soluble polymer having an anionic group) was used as the electrophoresis buffer solution. Either of the samples was injected into the migration path from one end, and subjected to electrophoresis at a voltage of 0.8 kV to measure absorbance at 415 nm. The electropherogram obtained by the measurement of the healthy human blood was similar to that shown in FIG. 6. The electropherogram obtained by the measurement of the sample containing the modified Hb is similar to that shown in FIG. 7.

The modified Hb separation performance test and the within-run reproducibility test were performed using the measurement samples prepared in the process (2) by the same methods as in the processes (5) and (6) of Example 1, respectively. Table 5 and Table 6 show the respective results.

Example 9

(1) Coating of Inner Surface of Migration Path

A double-T-shaped electrophoresis migration path having a width of 80 μm was formed on a microdevice made of polydimethylsiloxane (7 cm×5 cm). In order to wash the inside of the migration path, 0.1N NaOH, ion exchange water, and 0.2N HCl were allowed to flow through the migration path on the microdevice in this order. Thereafter, a polymer aqueous solution containing 1.0% by weight of a copolymer including 2-hydroxyethyl methacrylate (produced by Wako Pure Chemical Industries, Ltd., non-ionic hydrophilic polymer) was allowed to flow through the migration path for 20 minutes. Subsequently, air was injected into the migration path to send out the polymer aqueous solution, and then the migration path was dried in a drier at a temperature of 40° C. for 12 hours. Thereafter, the procedure of injection of the polymer aqueous solution, injection of air and drying was repeated 5 times to coat with the non-ionic hydrophilic polymer.

Next, the procedure of solution flow through, injection of air and drying was repeated 5 times by the same method as that described above to further coat the inner surface of the capillary with a cationic polymer, except that 0.2N hydrochloric acid containing 2.0% by weight of chitosan (produced by Wako Pure Chemical Industries, Ltd., ionic hydrophilic polymer) instead of the polymer solution containing 1.0% by weight of the copolymer including 2-hydroxyethyl methacrylate.

(2) Preparation of Measurement Sample

A healthy human blood sample and a sample containing the modified Hb were prepared by the same method as in Example 7.

(3) Measurement by Electrophoresis

The prepared healthy human sample and the sample containing the modified Hb thus prepared were measured using the above-mentioned migration path. A 300 mM malate buffer solution (pH 5.2) containing 1.7% by weight of a 2-acrylamide-2-methylpropanesulfonic acid copolymer (produced by TOAGOSEI Co., Ltd., water-soluble polymer having an anionic group) was used as the electrophoresis buffer solution. Either of the samples was injected into the migration path from one end, and subjected to electrophoresis at a voltage of 1.0 kV to measure absorbance at 415 nm. The electropherogram obtained by the measurement of the healthy human blood sample was similar to that shown in FIG. 6. The electropherogram obtained by the measurement of the sample containing the modified Hb is similar to that shown in FIG. 7.

The modified Hb separation performance test and the within-run reproducibility test were performed by the same methods as in the processes (5) and (6) of Example 1, respectively. Table 5 and Table 6 show the respective results.

Comparative Example 4

In Comparative Example 4, the non-ionic hydrophilic polymer and the cationic polymer used in Examples 7 to 9 were used for coating but in the reverse order. Namely, an inner surface of a migration path was coated with the cationic polymer, and then coated with the non-ionic polymer.

(1) Coating of Inner Surface of Migration Path

A capillary made of fused silica (produced by GL Sciences, Inc., 75 μm in inside diameter×50 cm in full length) was set in a capillary electrophoresis apparatus (produced by Beckman Coulter, Inc., PAC/E MDQ). In order to wash the inside of the capillary, 0.2N NaOH, ion exchange water, and 0.5N HCl were allowed to flow through the capillary in this order. Thereafter, a 5.0% by weight aqueous solution of polybrene (produced by Wako Pure Chemical Industries, Ltd., cationic polymer) was allowed to flow through the capillary for 20 minutes. Subsequently, air was injected into the capillary to send out the polybrene aqueous solution, and then the capillary was dried in a drier at a temperature of 40° C. for 12 hours. Thereafter, the procedure of injection of the polybrene aqueous solution, injection of air and drying was repeated 5 times to coat the inner surface of the capillary with the cationic polymer.

A 1.0% by weight aqueous solution of polyvinyl alcohol (produced by Nihon Synthetic Chemical Industry Co. Ltd., GOHSENOL GH-20, non-ionic hydrophilic polymer) was allowed to flow through the prepared capillary for 20 minutes by the same method as that described above. Subsequently, air was injected into the capillary to send out the polyvinyl alcohol aqueous solution, and then the capillary was dried in a drier at a temperature of 40° C. for 12 hours. Thereafter, the procedure of injection of the polyvinyl alcohol aqueous solution, injection of air and drying was repeated 5 times to coat the cationic polymer (polybrene) coating the inner surface of the capillary with the non-ionic hydrophilic polymer.

(2) Preparation of Measurement Sample

A healthy human sample and a sample containing the modified Hb were prepared by the same method as in Example 7.

(3) Measurement by Electrophoresis

The same electrophoresis buffer solution as that used in Example 7 was used as the electrophoresis buffer solution. Either of the samples was injected into the capillary from one end, and subjected to electrophoresis at a voltage of 20 kV to measure absorbance at 415 nm. No hemoglobin peak was found in either of the results of the healthy human blood sample and the sample containing the modified Hb. Accordingly, the results show that without the cationic innermost surface, hemoglobin cannot be measured.

TABLE 5

| | ΔHbA1c value (%) (Sample containing modified Hb - Healthy human sample) | |
|---|---|---|
| | Sample containing unstable HbA1c | Sample containing carbamylated Hb |
| Example 7 | 0.1 | 0.1 |
| Example 8 | 0.0 | 0.1 |
| Example 9 | −0.1 | 0.1 |

Table 5 shows that the ΔHbA1c values obtained under the respective measurement conditions of Examples 7 and 8 were remarkably small. Accordingly, the results show that stable HbA1c can be accurately measured under the measurement conditions of Examples 7 and 8 even under the presence of modified Hbs.

TABLE 6

| | Within-run reproducibility test CV (%) |
|---|---|
| Example 7 | 1.02 |
| Example 8 | 0.99 |
| Example 9 | 1.05 |

As shown in Table 6, the CV values indicating the data variation obtained by the within-run reproducibility test under the respective measurement conditions of Examples 7 and 8 were as good as about 1%.

Example 10

A migration path with a cationic polymer immobilized thereon filled with an ion exchanger was used, and a buffer solution containing a water-soluble acrylic polymer having an anionic group was used as the electrophoresis buffer solution for measurement in Example 10.

(1) Preparation of Ion Exchanger

To 2.0 L of 4% polyvinyl alcohol aqueous solution was added a mixture containing 300 g of tetraethylene glycol dimethacrylate (non-ionic monomer, produced by Shin-Nakamura Chemical Co., Ltd), 50 g of 2-hydroxymethyl methacrylate (non-ionic monomer, produced by Shin-Nakamura Chemical Co., Ltd), 100 g of diethylaminoethyl methacrylate (monomer containing an amino group, produced by Wako Pure Chemical Industries, Ltd.), and 1.0 g of benzoyl peroxide. The obtained mixture was heated to 80° C. under stirring in a nitrogen atmosphere for 10 hours to allow polymerization to proceed. The obtained polymer was washed and retrieved. Thus, an ion exchanger having an amino group was obtained.

(2) Preparation of Migration Path

A cross-shaped open channel having a size of 100 μm in width×70 mm in length was formed on an electrophoresis microdevice made of polydimethylsiloxane (50 mm×100 mm). The open channel was used as the migration path. The formed migration path was coated using a chitosan solution by the same method as in Example 2, and filled with the ion exchanger having an amino group prepared in the ion exchanger preparation process (1).

(3) Measurement of Healthy Human Blood Sample and Sample Containing Modified Hb

The healthy human blood sample and the sample containing the modified Hb were measured by the same method as in Example 8, except that a citrate buffer solution (pH 4.7) containing 2.0% by weight of chondroitin sulfate was used as the electrophoresis buffer solution, and that the samples were subjected to electrophoresis at a voltage of 1000 V.

The electropherogram obtained by the measurement of the healthy human blood sample was similar to that shown in FIG. 4. The electropherogram obtained by the measurement of the sample containing the modified Hb was similar to that shown in FIG. 5.

Example 11

A migration path with an ozonized inner surface was used for measurement in each of Examples 11 to 13.

(1) Preparation of Migration Path

A capillary made of fused silica (produced by GL Sciences, Inc., 25 μm in inside diameter×30 cm in full length) was set in a capillary electrophoresis apparatus (PAC/E MDQ, produced by Beckman Coulter, Inc.). In order to wash the inside of the capillary, a 0.2N NaOH aqueous solution, ion exchange water, and a 0.5N HCl aqueous solution were allowed to flow through the capillary in this order. Thereafter, a 0.2N hydrochloric acid solution containing 0.5% by weight of chitosan was allowed to flow through the capillary for 20 minutes. Subsequently, air was injected into the capillary to send out the chitosan solution, and then the capillary was dried in a drier at a temperature of 40° C. for 12 hours. Subsequently, the procedure of injection of the chitosan solution, injection of air, and drying was repeated 5 times. The prepared capillary was filled with ozone water having a dissolved ozone gas concentration of 100 ppm, and allowed to stand. After 10 minutes standing, the ozone water was sucked up, and the same ozone water was injected again. Thereafter, the capillary was allowed to stand for 10 minutes. Thus, the capillary having the migration path ozonized with ozone water was prepared. The prepared capillary was filled with a 150 mM citrate buffer solution (pH 5.2) containing 2.0% by weight of chondroitin sulfate.

(2) Measurement of Healthy Human Blood Sample

A blood sample was collected from a healthy human with heparin. To 100 μL of the healthy human whole blood sample was added 150 μL of a citrate buffer solution (pH 6.0) containing 0.05% by weight of Triton X-100 (surfactant, produced by Wako Pure Chemical Industries, Ltd.) to hemolyze and dilute the blood sample. The diluted blood sample thus obtained was used as a diluted healthy human blood sample.

The diluted blood sample was injected into the capillary ozonized with ozone water from one end, and subjected to electrophoresis by applying a voltage of 25 kV to both ends of the capillary to measure transition of visible light absorbance at 415 nm. Thus, stable HbA1c in the human blood was measured.

The electropherogram obtained by the measurement of the healthy human blood sample was similar to that shown in FIG. 6.

(3) Measurement of Sample Containing Modified Hb

To the healthy human whole blood sample used in the measurement of the healthy human blood was added glucose to give a concentration of 2500 mg/dL, and warmed at a temperature of 37° C. for 3 hours to artificially prepare a sample containing a large amount of unstable HbA1c that is a form of modified Hbs. The sample containing the modified Hb was measured by the same method as in the measurement of the healthy human blood sample.

The electropherogram obtained by the measurement of the sample containing the modified Hb was similar to that shown in FIG. 7.

Example 12

(1) Preparation of Migration Path

A migration path having a length of 75 mm and a width of 60 μm was formed on a microdevice made of polydimethylsiloxane. Thus, the cross-shaped electrophoresis microdevice was prepared. The migration path was filled with a 0.5% by weight aqueous solution of polybrene, and allowed to stand for 20 minutes. Subsequently, air was injected into the migration path to send out the polybrene aqueous solution, and then the migration path was dried in a drier at a temperature of 40° C. for 12 hours. Thereafter, the procedure of injection of the polybrene aqueous solution, injection of air and drying was repeated 5 times. Thus, the electrophoresis microdevice having the coated migration path was obtained. In addition, the electrophoresis microdevice having the migration path thus coated was ozonized with ozone water by the same method as in Example 11. Thus, the electrophoresis microdevice ozonized with ozone water was prepared. The migration path thus ozonized with ozone water of the electrophoresis microdevice was filled with a 50 mM succinate buffer solution (pH 5.8) containing 1.5% by weight of dextran sulfate.

(2) Measurement of Healthy Human Blood Sample and Sample Containing Modified Hb

The samples were measured by following the same procedure as in the healthy human blood measurement process (2) and the sample containing the modified Hb measurement process (3) of Example 11, respectively. Here, the samples were subjected to electrophoresis using the electrophoresis microdevice thus ozonized with ozone water by applying a voltage of 500 V to both ends of the migration path to measure transition of visible light absorbance at 415 nm. The electropherogram obtained by the measurement of the healthy human blood sample was similar to that shown in FIG. 6. The electropherogram obtained by the measurement of the sample containing the modified Hb was similar to that shown in FIG. 7.

(3) Yield Test

An all-peak area value in the electropherogram obtained by the measurement of the healthy human blood sample under the measurement conditions of Example 12 was calculated. A relative value of the all-peak area value of Example 12 with respect to an all-peak area value of Example 11 as 100 was calculated.

Table 7 shows the results.

Example 13

(1) Preparation of Migration Path

A migration path having a length of 90 mm and a width of 50 μm was formed on a microdevice made of fused silica. Thus, the electrophoresis microdevice was prepared. The migration path was filled with a 0.2N hydrochloric acid solution containing 0.5% by weight of chitosan, and allowed to stand for 20 minutes. Thereafter, air was injected into the migration path to send out the chitosan solution, and then the migration path was dried in a drier at a temperature of 40° C. for 12 hours. Subsequently, the procedure of injection of the chitosan solution, injection of air, and drying were repeated 5 times. Thus, the electrophoresis microdevice having the coated migration path was prepared. The migration path thus coated of the electrophoresis microdevice was further ozonized with ozone water by the same method as in Example 1. Thus, the microdevice ozonized with ozone water was prepared. The migration path of the electrophoresis microdevice thus ozonized with ozone water was filled with a 100 mM phosphate buffer solution (pH 5.5) containing 2.0% by weight of chondroitin sulfate.

(2) Measurement of Healthy Human Blood Sample and Sample Containing Modified Hb

The healthy human blood sample and the sample containing the modified Hb were measured by the same method as in Example 2, except that the samples were subjected to electrophoresis using the electrophoresis microdevice ozonized with ozone water by applying a voltage of 700 V to both ends of the migration path. The electropherogram obtained by the measurement of the healthy human blood sample was similar to that shown in FIG. 6. The electropherogram obtained by the measurement of the sample containing the modified Hb was similar to that shown in FIG. 7.

(3) Yield Test

The yield test was performed by the same method as in the process (3) of Example 12. Table 7 shows the results.

Comparative Examples 5 to 7

The migration path was formed by the same method as in Examples 11 to 13, except that ozonization with ozone water was not performed, and a sample containing the modified Hb was measured.

The yield test was performed by the same method as in the process (3) of Example 12. Table 7 shows the results.

TABLE 7

|  | Yield test | |
|---|---|---|
|  | All-peak area value (count) | Relative value (%) |
| Example 11 | 549987 | 100.0 |
| Example 12 | 539876 | 98.2 |
| Example 13 | 550402 | 100.1 |
| Comparative Example 5 | 382671 | 69.6 |
| Comparative Example 6 | 402277 | 73.1 |
| Comparative Example 7 | 398660 | 72.5 |

AS shown in Table 7, all-peak area values of Examples 12 and 13 were equivalent to the all-peak area value of Example 11. However, all-peak area values of Comparative Examples 5 to 7 were smaller compared to the all-peak area values of Examples 11 to 13. This may be because some hemoglobin components non-specifically adsorb on the inner surface of the migration path under the measurement conditions of Comparative Examples 5 to 7 in which the migration path was not ozonized.

Example 14

A migration path coated with a cationic polymer immobilized thereon was used, and a buffer solution containing a water-soluble polymer having an anionic group and a chaotropic compound were used as the buffer solution for measurement in each of Examples 14 to 16.

(1) Coating of Migration Path

First, 0.5N hydrochloric acid solution containing 0.5% by weight of chitosan (chitosan-100, produced by Wako Pure Chemical Industries, Ltd.) as a cationic polymer was prepared. Next, 0.2N—NaOH, ion exchange water, and 0.5N—HCl were allowed to flow through a capillary made of fused silica (produced by GL Sciences, Inc., 25 μm in inside diameter×30 cm in full length) in this order to wash the inside of the capillary, and then the prepared chitosan solution was allowed to flow through the capillary for 20 minutes. Thereafter, air was injected into the capillary to send out the chitosan solution, and then the capillary was dried in a drier at a temperature of 40° C. for 12 hours. Subsequently, the chitosan solution was injected again, and the procedure of injection of air and drying was repeated 5 times.

The chitosan immobilized capillary thus prepared was set in a capillary electrophoresis apparatus (PAC/E MDQ, produced by Beckman Coulter, Inc.).

(2) Preparation of Buffer Solution

A malate buffer solution (pH 4.8) containing 1.0% by weight of sodium nitrate as the chaotropic compound and 2.0% by weight of chondroitin sulfate as the water-soluble polymer having an anionic group was prepared as the buffer solution.

(3) Measurement of Healthy Human Blood Sample

A blood sample was collected from a healthy human with heparin. To 70 μL of the healthy human whole blood sample was added 200 μL of a citrate buffer solution (pH 6.0) containing 0.05% Triton X-100 (surfactant, produced by Wako Pure Chemical Industries, Ltd.) to hemolyze and dilute the blood sample. The sample thus obtained was used as a measurement sample.

The sample was injected into the capillary from one end, and subjected to electrophoresis by applying a voltage of 20 kV to the buffer solutions set for the ends of the capillary to measure transition of visible light absorbance at 415 nm. Thus, stable HbA1c in the human blood was measured by capillary electrophoresis.

(4) Measurement of Sample Containing Modified Hb

To the healthy human whole blood sample used in the measurement of the healthy human blood sample was added glucose to give a concentration of 2500 mg/dL. Thus, a sample containing a large amount of unstable HbA1c that is a form of modified Hbs was artificially prepared. The sample was injected into the capillary from one end, and subjected to electrophoresis by applying a voltage of 20 kV to the buffer solutions set for the ends of the capillary to measure transition of visible light absorbance at 415 nm. Thus, stable HbA1c in the human blood was measured by capillary electrophoresis. The electropherogram obtained by the measurement of the healthy human blood sample was similar to that shown in FIG. 6. The electropherogram obtained by the measurement of the sample containing the modified Hb was similar to that shown in FIG. 7.

(5) Modified Hb Separation Performance Test and Within-Run Reproducibility Test

The modified Hb separation performance test and the within-run reproducibility test were performed using the samples prepared in the processes (3) and (4) by the same methods as in the processes (5) and (6) of Example 1, respectively. Table 8 and Table 9 show the respective results.

Example 15

An inner surface of a capillary was coated by the same method as in Example 1, except that a 0.5% by weight aqueous solution of polybrene (produced by Wako Pure Chemical Industries, Ltd.) as the cationic polymer was used. Thus, an electrophoresis apparatus was prepared.

An amount of 3.0 g of acrylamide-2-methylpropane-sulfonic acid (produced by Wako Pure Chemical Industries, Ltd.) as the acrylic monomer having an anionic group, and 2.0 g of hydroxyethyl methacrylate (produced by Wako Pure Chemical Industries, Ltd.) as the acrylic monomer without anionic groups are dissolved in 50 mL of ion exchange water. To the solution thus obtained was added 0.05 g of potassium persulfate, and the solution was heated to 80° C. under stirring in a nitrogen atmosphere to allow polymerization to proceed. The whole mixture obtained by 10 hour polymerization was poured into a dialysis tube (produced by Sanko Junyaku Co., Ltd., UC C65-50), and dialyzed in ion exchange water for 12 hours to obtain an water-soluble acrylic polymer having an anionic group.

A malate buffer solution (pH 4.7) containing 1.0% by weight of sodium perchlorate as the chaotropic compound and 2.0% by weight of the water-soluble polymer having an anionic group was prepared.

The healthy human blood sample and the sample containing the modified Hb were measured by the same method as in Example 1, except that the electrophoresis apparatus and the buffer solution prepared above were used. The electropherogram obtained by the measurement of the healthy human blood sample was similar to that shown in FIG. 6. The electropherogram obtained by the measurement of the sample containing the modified Hb was similar to that shown in FIG. 7.

The modified Hb separation performance test and the within-run reproducibility test were performed by the same methods as in the process (5) of Example 14. Table 8 and Table 9 show the respective results.

Example 16

A cross-shaped migration path was formed on a microdevice made of polydimethylsiloxane (50 mm×75 mm×3 mm), and a buffer solution reservoir was set for each end of the migration path.

The migration path was coated by the same method as in Example 1, except that chitosan (0.5% by weight, in a 0.5N hydrochloric acid solution) as the ionic polymer was used.

The healthy human blood sample and the sample containing the modified Hb were measured by the same method as in Example 1, except that a malate buffer solution (pH 4.8) containing 5.0% by weight of urea as the chaotropic compound and 2.0% by weight of chondroitin sulfate as the water-soluble polymer having an anionic group was used, and the samples were subjected to microdevice electrophoresis at a voltage of 1000 V.

The electropherogram obtained by the measurement of the healthy human blood sample was similar to that shown in FIG. 6. The electropherogram obtained by the measurement of the sample containing the modified Hb was similar to that shown in FIG. 7.

The modified Hb separation performance test and the within-run reproducibility test were performed by the same methods as in the process (5) of Example 14. Table 8 and Table 9 show the respective results.

Comparative Example 8

The healthy human blood sample and the sample containing the modified Hb were measured by the same method as in Example 14, except that no chaotropic compound was used.

The modified Hb separation performance test and the within-run reproducibility test were performed by the same methods as in the process (5) of Example 14. Table 8 and Table 9 show the respective results.

TABLE 8

|  | ΔHbA1c value (%) (Sample containing modified Hb - Healthy human sample) | |
|---|---|---|
|  | Sample containing unstable HbA1c | Sample containing carbamylated Hb |
| Example 14 | 0.0 | 0.2 |
| Example 15 | 0.2 | 0.1 |
| Example 16 | 0.0 | −0.1 |
| Comparative Example 8 | 0.5 | −1.4 |

As shown in Table 8, the ΔHbA1c values obtained under the respective measurement conditions of Examples 14 to 16 were remarkably small. Accordingly, the results show that stable HbA1c can be accurately measured under the measurement conditions of Examples 14 to 16 even under the presence of modified Hbs. However, the ΔHbA1c value obtained by the measurement under the conditions of Comparative Example 8 was large. Accordingly, the results show that the measurement under the conditions of Comparative Example 8 was susceptible to modified Hbs.

TABLE 9

|  | Within-run reproducibility test CV (%) |
|---|---|
| Example 14 | 0.92 |
| Example 15 | 1.03 |
| Example 16 | 0.98 |
| Comparative Example 8 | 3.32 |

As shown in Table 9, the CV values indicating the data variation obtained by the within-run reproducibility test of Examples 14 to 16 were as good as about 1%. On the contrary, the CV value indicating the data variation obtained by the within-run reproducibility test under the measurement conditions of Comparative Example 8 was unfavorably over 3%.

Example 17

A migration path coated with a cationic polymer immobilized thereon was used, and a buffer solution containing a water-soluble polymer having an anionic group and a nitrite was used as the buffer solution for measurement in each of Examples 17 to 20.
(1) Preparation of Migration Path
A 0.2N hydrochloric acid solution containing 0.2% by weight of chitosan (produced by Wako Pure Chemical Industries, Ltd., chitosan 100) as the anionic polymer was prepared. Next, 0.2N—NaOH, ion exchange water, and 0.5N—HCl were allowed to flow through a capillary made of fused silica (produced by GL Sciences, Inc., 25 μm in inside diameter×30 cm in full length) in this order to wash the inside of the capillary, and then the prepared chitosan solution was allowed to flow through the capillary for 20 minutes. Subsequently, air was injected into the capillary to send out the chitosan solution, and then the capillary was dried in a drier at a temperature of 40° C. for 12 hours. Thereafter, the chitosan solution was injected again, and the procedure of injection of air and drying was repeated 5 times.

The chitosan immobilized capillary thus prepared was set in a capillary electrophoresis apparatus (produced by Beckman Coulter, Inc., PAC/E MDQ). Subsequently, a citrate buffer solution (pH 4.8) containing 50 mM sodium nitrite (nitrite, produced by Wako Pure Chemical Industries, Ltd.) and 2.0% by weight of chondroitin sulfate (produced by Wako Pure Chemical Industries, Ltd.) was used as the electrophoresis buffer solution, and set for both ends of the capillary to fill the capillary with the buffer solution.
(2) Measurement of Healthy Human Blood Sample
A blood sample was collected from a healthy human with sodium fluoride. To 70 μL of the healthy human whole blood sample was added 200 μL of a citrate buffer solution (pH 6.0) containing 0.05% by weight of Triton X-100 and 20 mM sodium nitrite at to hemolyze and dilute the blood sample. The sample thus obtained was used as a measurement sample.
The sample was injected into the capillary from one end, and subjected to electrophoresis by applying a voltage of 20 kV to the buffer solutions set for the ends of the capillary to measure transition of visible light absorbance at 415 nm. Thus, stable HbA1c in the human blood was measured by capillary electrophoresis. The electropherogram obtained by the measurement of the healthy human blood sample was similar to that shown in FIG. 6.
(3) Measurement of Sample Containing Modified Hb
To the healthy human whole blood sample used in the measurement of the healthy human blood sample was added glucose (produced by Wako Pure Chemical Industries, Ltd.) to give a concentration of 2000 mg/dL, and warmed at a temperature of 37° C. for 3 hours to artificially prepare a sample containing a large amount of unstable HbA1c that is a form of modified Hbs. The electropherogram obtained by the measurement of the sample containing the modified Hb was similar to that shown in FIG. 7.
(4) Evaluation by Between-Run Reproducibility Test
One healthy human blood sample was continuously measured five times in a day for consecutive 5 days under the measurement conditions of Example 17. The CV value of the stable HbA1c values was calculated using the obtained electropherograms. Table 10 shows the results.

Example 18

A healthy human blood sample and a sample containing the modified Hb were measured by capillary electrophoresis by following the same procedure as in Example 17, except that an inner surface of a capillary was coated using a 0.5% by weight aqueous solution of polybrene (produced by Nacalai Tesque, Inc.) as the cationic polymer by the same method as in Example 17, and that a malate buffer solution (pH 4.8) containing 30 mM sodium nitrite and 2.0% by weight of chondroitin sulfate was used as the electrophoresis buffer solution.
The obtained electropherograms were similar to those shown in FIGS. 6 and 7.
Table 10 shows the results of the between-run reproducibility test performed by following the same procedure as in Example 17.

Example 19

A cross-shaped migration path (flow channel width: 100 μm) was formed on a microdevice made of glass (50 mm in width×30 mm in length×2 mm in thickness), and a buffer solution reservoir was set for each end of the migration path.
The migration path was coated with chitosan (1.0% by weight aqueous solution) that is the cationic polymer by the same method as in Example 17. Then, the healthy human blood sample and the sample containing the modified Hb were measured by microdevice electrophoresis at a voltage of 1000 V using the same buffer solution as that used in Example 17.

The obtained electropherograms were similar to those shown in FIGS. 6 and 7.

Table 10 shows the results of the between-run reproducibility test performed by following the same procedure as in Example 17.

Example 20

A double-T-shaped migration path (flow channel width: 80 μm) was formed on a microdevice made of polydimethylsiloxane (50 mm in width×30 mm in length×2 mm in thickness), and a buffer solution reservoir was set for each end of the migration path. The migration path was coated with polybrene (1.0% by weight aqueous solution) that is the cationic polymer by the same method as in Example 17. Subsequently, the healthy human blood sample and the sample containing the modified Hb were measured by microdevice electrophoresis at a voltage of 900 V using the same electrophoresis buffer solution as that used in Example 18.

The obtained electropherograms were similar to those shown in FIGS. 6 and 7.

Table 10 shows the results of the between-run reproducibility test performed by following the same procedure as in Example 17.

Comparative Examples 9 to 12

In each of Comparative Examples 9 to 12, a healthy human blood sample and a sample containing the modified Hb were measured by following the same procedure as in Examples 17 to 20, except that an electrophoresis buffer solution and a hemolysing agent without nitrites were used.

Table 10 shows the results of the between-run reproducibility test performed by following the same procedure as in Example 17.

TABLE 10

| | Stable HbA1c value (%) (average, n = 5) | | | | | | Standard deviation | CV value (%) |
|---|---|---|---|---|---|---|---|---|
| | Day 1 | Day 2 | Day 3 | Day 4 | Day 5 | Average | | |
| Example 17 | 4.4 | 4.5 | 4.5 | 4.6 | 4.5 | 4.5 | 0.07 | 1.6 |
| Example 18 | 4.5 | 4.5 | 4.5 | 4.4 | 4.5 | 4.5 | 0.04 | 1.0 |
| Example 19 | 4.6 | 4.5 | 4.5 | 4.6 | 4.5 | 4.5 | 0.05 | 1.2 |
| Example 20 | 4.5 | 4.4 | 4.5 | 4.6 | 4.5 | 4.5 | 0.07 | 1.6 |
| Comparative Example 9 | 4.5 | 4.3 | 4.7 | 4.8 | 4.5 | 4.6 | 0.19 | 4.3 |
| Comparative Example 10 | 4.8 | 4.3 | 4.5 | 4.5 | 4.7 | 4.6 | 0.19 | 4.3 |
| Comparative Example 11 | 4.8 | 4.3 | 4.5 | 4.8 | 4.6 | 4.6 | 0.21 | 4.6 |
| Comparative Example 12 | 4.4 | 4.4 | 4.5 | 4.8 | 4.1 | 4.4 | 0.25 | 5.7 |

As shown in Table 10, the CV values indicating the between-run reproducibility of the stable HbA1c values of the respective healthy human blood samples obtained in Examples 17 to 20 were 1.6%. The results show that stable HbA1c value could be measured with sufficient accuracy in Examples 17 to 20. On the contrary, the CV values obtained in Comparative Examples 9 to 12 were over 4%, which are remarkably large. Accordingly, the results show that it was impossible to accurately measure in Comparative Examples 9 to 12.

Example 21

A migration path made of a cationic material was used, and a buffer solution containing a water-soluble polymer having an anionic group was used as the electrophoresis buffer solution for measurement in each of Examples 21 to 23.

A microdevice (50 mm×80 mm) was formed by using a terpolymer (diethylaminoethyl methacrylate (monomer having a cationic group))-(2-hydroxyethyl methacrylate)-(methyl methacrylate). A flow channel (100 μm inside diameter× 50 mm) was formed on the obtained microdevice.

A citrate buffer solution (pH 5.0) containing 2.0% by weight of chondroitin sulfate (anionic polymer) was injected into the flow channel as the buffer solution.

A blood sample was collected from a healthy human with sodium fluoride. To 70 μL of the healthy human whole blood sample was added 200 μL of a citrate buffer solution (pH 6.0) containing 0.5% by weight of saponin to hemolyze and dilute the blood sample. The sample thus obtained (healthy human sample) was used.

(Measurement Of Healthy Human Sample)

The obtained healthy human sample was injected into the flow channel, and subjected to electrophoresis by applying a voltage of 800 V to both ends of the flow channel. A portion on the migration path was irradiated with visible light at 415 nm, and transition of absorbance of the transmitted light was measured. The obtained electropherogram was similar to that shown in FIG. 6.

(Modified Hb Separation Performance Test)

To the healthy human whole blood sample was added glucose to give a concentration of 2000 mg/dL. Thus, a sample containing a large amount of unstable HbA1c (L-A1c sample) was artificially prepared. To the healthy human whole blood sample was added sodium cyanate to give a concentration of 50 mg/dL. Thus, a sample containing a large amount of a carbamylated Hb (CHb sample) was artificially prepared.

The L-A1c sample and the CHb sample were measured, and the obtained electropherograms were similar to that shown in FIG. 7.

Example 22

The healthy human sample, the L-A1c sample and the CHb sample were measured by following the same procedure as in Example 1, except that a microdevice was prepared using acrylamide as the monomer having a cationic group, and a phosphate buffer solution (pH 5.4) containing 1.5% by weight of dextran sulfate was used as a buffer solution. The obtained electropherograms were similar to those shown in FIGS. 6 and 7.

Example 23

The healthy human sample, the L-A1c sample and the CHb sample were measured by following the same procedure as in Example 1, except that a microdevice was prepared using a terpolymer (ethylene imine (monomer having a cationic group))-(ethylene vinyl alcohol)-(methyl methacrylate), and a malate buffer solution (pH 4.9) containing 1.0% by weight of a copolymer (2-(meth)acrylamide-2-methylpropanesulfonic acid)-(2-hydroxyethyl methacrylate) was used as the buffer solution. The obtained electropherograms were similar to those shown in FIGS. 6 and 7.

Example 24

A microdevice having a migration path coated with a cationic polymer immobilized thereon or a migration path made of a cationic material was used, and a buffer solution containing a water-soluble polymer having an anionic group was used as the electrophoresis buffer solution for measurement in each of Examples 24 to 26. The migration path of the used microdevice had been filled with the buffer solution in advance. Abnormal hemoglobins were also measured using the device.
(Production of Device Supporting Unit and Other Components)
A measurement system of hemoglobin was assembled based on the schematic view shown in FIG. 2.
Absorbance at 415 nm was measured using a multi-channel high-voltage sequencer power supply device (produced by LabSmith, HVS448), a 50 W halogen light source device (produced by Moritex Corp., MHF-V501) and a spectroscope (produced by B&W Tek, Inc., CCD spectroscope, BTC112) as the power supply device and the light source and the detector, respectively. The obtained data of the absorbance at 415 nm was processed according to a self-made program.
A device supporting unit made of Teflon (registered trademark) designed to have a size fit for a microdevice described below was produced. Platinum electrodes (1 mm in diameter×20 mm in length) were attached to the obtained device supporting unit. The platinum electrodes were connected to the power supply device via a power cable. All other parts were self-made.
(Preparation of Microdevice)
A cross-shaped electrophoresis microdevice made of fused silica (outside dimensions: 50 mm×80 mm) was prepared. A linear migration path having a size of 100 μm in inside diameter×50 mm in length was formed on the microdevice.
A 0.5N sodium hydroxide aqueous solution, distilled water, a 0.5N hydrochloric acid aqueous solution, and distilled water were sequentially allowed to flow through a flow channel on the microdevice to wash the inside of the flow channel. Subsequently, the flow channel was filled with a 0.5N hydrochloric acid solution containing 0.5% by weight of chitosan (chitosan 100, cationic polymer, produced by Wako Pure Chemical Industries, Ltd.). The flow channel was allowed to stand at room temperature for 30 minutes, and then air was injected into the flow channel to send out the chitosan solution from the flow channel. Thereafter, the flow channel was warmed at a temperature of 40° C. for 5 hours.
Next, the flow channel including the migration path thus coated with the cationic polymer of the microdevice was filled with a citrate buffer solution (pH 5.0) containing 2.0% by weight of chondroitin sulfate (anionic polymer, produced by Nacalai Tesque, Inc.). Thus, the microdevice having the migration path filled with the buffer solution was prepared.
(Preparation and Measurement of Healthy Human Sample)
A blood sample collected from a healthy human with sodium fluoride was used as a healthy human whole blood sample. To 70 μL of the healthy human whole blood sample was added 200 μL of a citrate buffer solution (pH 6.0) containing 0.5% by weight of saponin (produced by Wako Pure Chemical Industries, Ltd.) to hemolyze and dilute the healthy human whole blood sample. The sample thus prepared was used as a healthy human sample.
The prepared healthy human sample was injected into the obtained flow channel of the microdevice, and subjected to electrophoresis by applying a voltage of 800 V to both ends of the flow channel. A portion on the migration path was irradiated with visible light at 415 nm, and transition of absorbance of the transmitted light was measured. The obtained electropherogram was similar to that shown in FIG. 6.
(Modified Hb Separation Performance Test)
To the healthy human whole blood sample was added glucose (produced by Wako Pure Chemical Industries, Ltd.) to give a concentration of 2000 mg/dL. Thus, a sample containing a large amount of unstable HbA1c (L-A1c sample) was artificially prepared. To the healthy human whole blood sample was added sodium cyanate (produced by Wako Pure Chemical Industries, Ltd.) to give a concentration of 50 mg/dL. Thus, a sample containing a large amount of a carbamylated Hb (CHb sample) was artificially prepared.
The L-A1c sample and the CHb sample thus prepared were measured by electrophoresis performed by following the same procedure as in the measurement of the healthy human sample, and the obtained electropherograms were similar to that shown in FIG. 7.

Example 25

A double-T shaped electrophoresis microdevice made of polydimethylsiloxane (outside dimensions: 50 mm×80 mm) was prepared. A linear migration path having a size of 100 μm in inside diameter×50 mm in length was formed on the microdevice.
A 0.1N sodium hydroxide aqueous solution, distilled water, a 0.1N hydrochloric acid aqueous solution, and distilled water were sequentially allowed to flow through a flow channel on the obtained microdevice to wash the inside of the flow channel. Subsequently, the flow channel was filled with a 0.5% by weight aqueous solution of polyvinyl alcohol (GOHSENOL GH20, produced by Nihon Synthetic Chemical Industry Co. Ltd.). The flow channel was allowed to stand at room temperature for 30 minutes, and then air was injected into the flow channel to send out the polyvinyl alcohol aqueous solution from the flow channel. Thereafter, the flow channel was warmed at a temperature of 40° C. for 5 hours. Next, the flow channel was filled with 4% by weight aqueous solution of polybrene (cationic polymer, produced by SIGMA-ALDRICH Japan K.K.). The flow channel was allowed to stand at room temperature for 30 minutes, and then air was injected into the flow channel to send out the polybrene aqueous solution from the flow channel. Thereafter, the flow channel was warmed at a temperature of 40° C. for 5 hours. The procedure of injection of the polybrene aqueous solution and warming was repeated 3 times for coating with the cationic polymer.
The obtained flow channel on the microdevice was filled with a phosphate buffer solution (pH 5.4) containing 1.5% by weight of dextran sulfate (produced by Wako Pure Chemical Industries, Ltd.). Thus, the microdevice having the flow channel filled with the buffer solution was prepared.

The healthy human sample, the L-A1c sample, and the CHb sample were measured by following the same procedure as in Example 24, except that a voltage of 900 V was applied. The electropherogram obtained by the measurement of the healthy human sample was similar to that shown in FIG. 6. The electropherograms obtained by the measurement of the L-A1c sample and the CHb sample were similar to that shown in FIG. 7.

Example 26

A cross-shaped electrophoresis microdevice (outside dimensions: 50 mm×80 mm) was produced using a terpolymer (diethylaminoethyl methacrylate (monomer having a cationic group))-(2-hydroxyethyl methacrylate)-(methyl methacrylate). A linear migration path with a size of 100 μm in inside diameter×50 mm in length was formed on the microdevice.

The obtained flow channel of the microdevice was filled with a malate buffer solution (pH 5.0) containing 1.5% by weight of chondroitin sulfate (produced by Wako Pure Chemical Industries, Ltd.). Thus, the microdevice having the flow channel filled with the buffer solution was prepared.

The healthy human sample, the L-A1c sample, and the CHb sample were measured by following the same procedure as in Example 24, except that a voltage of 900 V was applied. The electropherogram obtained by the measurement of the healthy human sample was similar to that shown in FIG. 6. The electropherograms obtained by the measurement of the L-A1c sample and the CHb sample were similar to that shown in FIG. 7.

Comparative Example 13

A cross-shaped electrophoresis microdevice made of fused silica (outside dimensions: 50 mm×80 mm) was produced. A linear migration path having a size of 100 μm in inside diameter×50 mm in length was formed on the microdevice.

A 0.5N sodium hydroxide aqueous solution, distilled water, a 0.5N hydrochloric acid aqueous solution, and distilled water were sequentially allowed to flow through a flow channel on the obtained microdevice to wash the inside of the flow channel. Subsequently, a 0.5N hydrochloric acid solution containing 0.5% by weight of chitosan (chitosan 100, cationic polymer, produced by Wako Pure Chemical Industries, Ltd.) was allowed to flow through the flow channel for 2 minutes to dynamically coat the flow channel.

Next, the flow channel including the migration path thus coated with the cationic polymer of the microdevice was filled with a citrate buffer solution (pH 5.0) containing 2.0% by weight of chondroitin sulfate (anionic polymer, produced by Nacalai Tesque, Inc.). Thus, the microdevice having the flow channel filled with the buffer solution was prepared.

The healthy human sample, the L-A1c sample, and the CHb sample were measured by following the same procedure as in Example 24. The electropherogram obtained by the measurement of the healthy human sample was similar to that shown in FIG. 6. The electropherograms obtained by the measurement of the L-A1c sample and the CHb sample were similar to that shown in FIG. 7.

(Abnormal Hb Separation Test)

A sample containing HbS and HbC (AFSC hemocontrol, produced by Helena Laboratories) as abnormal Hbs was measured in Example 24 by electrophoresis performed by following the same procedure as in the measurement of the healthy human sample. FIG. 9 shows the obtained electropherogram. In FIG. 9, the peak 1 represents stable HbA1c, the peak 2 represents HbAo, the peak 3 represents unstable HbA1c, the peak 4 represents HbF (fetal Hb), the peak 5 represents HbS, and, the peak 6 represents HbC. As shown in FIG. 9, stable HbA1c, HbS and HbC were favorably separated. The electropherograms obtained in Examples 25 and 26 and Comparative Example 13 were similar to that shown in FIG. 9.

A sample containing HbA2 (A2 control, level 2, produced by Bio-Rad Laboratories, Inc.) was measured in Example 24 by electrophoresis performed by following the same procedure as in the measurement of the healthy human sample. FIG. 10 shows the obtained electropherogram. In FIG. 10, the peak 1 represents stable HbA1c, the peak 2 represents HbAo, the peak 4 represents HbF (fetal Hb), and the peak 7 represents HbA2. As shown in FIG. 10, stable HbA1c and HbA2 were favorably separated. The electropherograms obtained in Examples 25 and 26 and Comparative Example 13 were similar to that shown in FIG. 10.

(Storage Stability Test)

The flow channels in the microdevices obtained in Examples 24 to 26 and Comparative Example 13 were filled with the above-mentioned citrate buffer solution (pH 5.0) containing 2.0% by weight of chondroitin sulfate (anionic polymer, produced by Nacalai Tesque, Inc.). The respective flow channels were sealed and left to stand at a temperature of 40° C. The microdevice were taken out after a certain period of time, and used for measurement of the healthy human sample by electrophoresis. FIG. 11 is a graph showing the relationship between the obtained stable HbA1c values (%) and the storage period.

As shown in FIG. 11, even after 20 days storage the microdevices produced in Examples 24 to 26 showed measurement performance equivalent to that shown immediately after the preparation. However, the microdevice of Comparative Example 13 showed poor stability, and could be used for measurement only immediately after coated. Accordingly, the results show that the migration path pre-filled with the buffer solution in the measurement system of hemoglobin of the present invention can avoid the coating procedure when used, and stably stored for a certain period of time after filled with the buffer solution. However, the results also show that the microdevice of Comparative Example 13 showed poor storage stability, and cannot be used as the microdevice having the migration path pre-filled with the buffer solution.

Example 27

A microdevice having a migration path coated with a cationic polymer immobilized thereon was used, and a buffer solution containing a water-soluble polymer having an anionic group was used as the electrophoresis buffer solution to analyze effects of the pH and the salt concentration of the buffer solution in each of Examples 27 and 28.

(1) Preparation of Microdevice

A migration path having a length of 80 mm and a width of 80 μm was formed on a cross-shaped device made of polydimethylsiloxane. Thus, the electrophoresis microdevice was prepared. The migration path was filled with a 0.5% chitosan solution (cationic polymer), and left to stand for 20 minutes. Subsequently, air was injected into the migration path to send out the chitosan solution, and then the migration path was dried in a drier at a temperature of 40° C. for 12 hours. Thereafter, the sequential procedure of injection of the chitosan solution, injection of air and drying was repeated 5 times. Thus, the microdevice having the coated migration path was prepared. The prepared migration path of the chitosan coated microdevice was filled with a 150 mM citrate buffer solution (pH 5.2) containing 2.0% chondroitin sulfate. Thus, the microdevice for measurement was prepared.

(2) Measurement of Healthy Human Blood Sample

A blood sample was collected from a healthy human with heparin. To 70 μL of the healthy human whole blood sample was added 200 μL of a citrate buffer solution (pH 6.0) containing 0.05% Triton X-100 (surfactant, produced by Wako Pure Chemical Industries, Ltd.) to hemolyze and dilute the blood sample. Thus, the hemolyzed sample was prepared.

The hemolyzed sample thus prepared was injected into one end of the migration path of the microdevice, and subjected to electrophoresis by applying a voltage of 1000 V to both ends of the migration path to measure transition of visible light absorbance at 415 nm. Thus, stable HbA1c was measured.

The obtained electropherogram was similar to that shown in FIG. 6.

(3) Measurement of Sample Containing Modified Hb

To the healthy human whole blood sample collected from a healthy human with heparin was added glucose to give a concentration of 2500 mg/dL, and warmed at a temperature of 37° C. for 3 hours to artificially prepare a sample containing a large amount of unstable HbA1c that is a form of modified Hb.

The hemolyzed sample thus prepared was injected into one end of the prepared migration path of the microdevice, and subjected to electrophoresis by applying a voltage of 1000 V to both ends of the migration path to measure transition of visible light absorbance at 415 nm. Thus, stable HbA1c was measured.

The obtained electropherogram was similar to that shown in FIG. 7.

Example 28

(1) Preparation of Microdevice

A migration path having a length of 50 mm and a width of 50 μm was formed on a device made of fused silica. Thus, the cross-shaped electrophoresis microdevice was prepared. The migration path was filled with a 0.5% polybrene aqueous solution, and allowed to stand for 20 minutes. Subsequently, air was injected into the migration path to send out the polybrene aqueous solution, and then the migration path was dried in a drier at a temperature of 40° C. for 12 hours. Thereafter, the procedure of injection of the polybrene aqueous solution, injection of air and drying was repeated 5 times. Thus, the microdevice having the migration path with the coated inner surface was prepared. The migration path of the polybrene coated microdevice was filled with a 50 mM succinate buffer solution (pH 5.8) containing 1.5% dextran sulfate. Thus, a microdevice for measurement was prepared.

(2) Measurement of Healthy Human Blood Sample and Sample Containing Modified Hb

The healthy human blood sample and the sample containing the modified Hb were measured by the same method as in Example 27, except that a voltage of 500 V was applied to both ends of the migration path for electrophoresis. The electropherogram obtained by the measurement of the healthy human blood sample was similar to that shown in FIG. 6. The electropherogram obtained by the measurement of the sample containing the modified Hb was similar to that shown in FIG. 7.

(3) pH and Salt Concentration Effect Test

The above-mentioned within-run reproducibility test was performed under the respective measurement conditions of Examples 27 and 28 using the citrate buffer solution used in Example 27 but at various pHs and various salt concentrations, and the succinate buffer solution used in Example 28 but at various pHs and various salt concentrations. Thus, the effects of the pH and the salt concentration of the buffer solutions were analyzed.

FIG. 12a shows the results obtained by changing the pHs, and FIG. 12b shows the results obtained by changing the salt concentrations.

As shown in FIGS. 12a and 12b, the CV values obtained under conditions of a pH of 5.0 to 6.0 and a salt concentration of 10 to 300 mM were small in both Examples 27 and 28. Accordingly the results show that stable HbA1c can be measured with high accuracy under those conditions.

A microdevice electrophoresis apparatus provided with a microdevice having a migration path coated with a cationic polymer immobilized thereon was used, and a buffer solution containing a water-soluble polymer having an anionic group was used as the electrophoresis buffer solution to analyze an effect of the applied measurement wavelength in Examples 29 and 30. A glucose measurement mechanism was installed on the above-mentioned electrophoresis apparatus, and glucose and stable HbA1c were simultaneously measured.

Example 29

(1) Preparation of Electrophoresis Apparatus

A migration path having a length of 80 mm and a width of 80 μm was formed on a chip made of polydimethylsiloxane. Thus, the cross-shaped electrophoresis microchip was prepared. The migration path was filled with a 0.5% chitosan solution, and left to stand for 20 minutes. Subsequently, air was injected into the migration path to send out the chitosan solution, and then the migration path was dried in a drier at a temperature of 40° C. for 12 hours. Thereafter, the procedure of injection of the chitosan solution, injection of air and drying was repeated 5 times. Thus, the microchip having the coated migration path was prepared. The migration path of the chitosan coated microchip was filled with a 150 mM citrate buffer solution (pH 5.2) containing 2.0% chondroitin sulfate. Thus, the microchip for measurement was prepared. The electrophoresis apparatus was assembled as follows: placing the obtained microchip for measurement on a support base having platinum electrodes (1 mm in diameter×5 mm in length); inserting the electrodes into reservoirs on the microchip; connecting the electrodes and the power supply unit (produced by LabSmith) via a voltage supply code; and setting a detector including a halogen lamp light source (produced by Moritex Corp., MHF-V501), a spectroscope (produced by B&W Tek, Inc., BTC112), and a computer for data processing on the microchip.

(2) Measurement of Healthy Human Blood Sample

A blood sample was collected from a healthy human with sodium fluoride. To 70 μL of the healthy human whole blood sample was added 200 μL of a citrate buffer solution (pH 6.0) containing 0.05% Triton X-100 (surfactant, produced by Wako Pure Chemical Industries, Ltd.) to hemolyze and dilute the blood sample. Thus, the hemolyzed healthy human blood sample was prepared.

The hemolyzed sample was injected into one end of the migration path of the obtained microchip, and subjected to electrophoresis by applying a voltage of 1000 V to both ends of the migration path to measure transition of visible light absorbance at a dominant wavelength of 415 nm and a subwavelength of 500 nm. Thus, stable HbA1c in the healthy human blood was measured.

The obtained electropherogram was similar to that shown in FIG. 6.

(3) Measurement of Sample Containing Modified Hb

To the healthy human whole blood sample collected from a healthy human with sodium fluoride was added glucose to give a concentration of 2500 mg/dL, and warmed at a temperature of 37° C. for 3 hours to artificially prepare a sample containing a large amount of unstable HbA1c that is a form of modified Hb. A hemolyzed sample containing the modified Hb was prepared by following the same procedure as in the process (2).

The hemolyzed sample containing the modified Hb was added to the reservoir formed on one end of the migration path of the microchip prepared in the process (1), and subjected to electrophoresis by applying a voltage of 1000 V to both ends of the migration path to measure transition of visible light absorbance at a dominant wavelength of 415 nm and a subwavelength of 500 nm. Thus, stable HbA1c in the sample containing the modified Hb was measured.

The obtained electropherogram was similar to that shown in FIG. 7.

Example 30

A migration path having a length of 50 mm and a width of 50 μm was formed on a microchip made of fused silica. Thus, the cross-shaped electrophoresis microchip was prepared. The migration path was filled with a 0.5% polybrene aqueous solution, and allowed to stand for 20 minutes. Subsequently, air was injected into the migration path to send out the polybrene aqueous solution, and then the migration path was dried in a drier at a temperature of 40° C. for 12 hours. Thereafter, the procedure of injection of the polybrene aqueous solution, injection of air and drying was repeated 5 times. Thus, the microchip having the coated migration path was prepared. The migration path of the polybrene coated microchip was filled with a 50 mM succinate buffer solution (pH 5.8) containing 1.5% dextran sulfate. Thus, a microchip for measurement was prepared. The healthy human blood sample and the sample containing the modified Hb were measured by the same method as in Example 1, except that the microchip for measurement thus prepared was used. The electropherogram obtained by the measurement of the healthy human blood sample was similar to that shown in FIG. 6. The electropherogram obtained by the measurement of the sample containing the modified Hb was similar to that shown in FIG. 7.

(Applied Wavelength Effect Test)

Measurement was performed under the respective measurement conditions of Examples 29 and 30 at various wavelengths applied (dominant wavelength and subwavelength). Specifically, absorbance at the dominant wavelength measured at a certain time period was subtracted by absorbance at the subwavelength measured at the same time, and the obtained value was plotted as absorbance at the time period to produce an electropherogram. The stable HbA1c value was calculated using the obtained electropherogram. Next, the above-mentioned within-run reproducibility test was performed to analyze the effect of the applied wavelength. Table 11 shows the results.

TABLE 11

| Applied wavelength (nm) | | CV value (%) | |
|---|---|---|---|
| Dominant wavelength | Subwavelength | Example 29 | Example 30 |
| 415 | — | 3.05 | 2.98 |
| 415 | 500 | 1.03 | 0.96 |
| 415 | 550 | 0.97 | 0.95 |

All the CV values determined in Examples 1 to 4 were about 3% when the stable HbA1c value were calculated using only the absorbance at the dominant wavelength of 415 nm without using the absorbance at the subwavelength. However, the CV values were about 1% when 500 nm or 550 nm were selected as the subwavelength, and the stable HbA1c values were calculated by subtraction of the absorbance at the subwavelength from the absorbance at the dominant wavelength of 415 nm. These results indicate that it is possible to measure at higher accuracy under these conditions.

(Simultaneous Measurement of Stable HbA1c and Glucose)

A migration path (length: 80 mm, width: 80 μm) similar to that shown in FIG. 3c was formed on the microchip made of polydimethylsiloxane used in Example 29. Here, the used electrodes for glucose measurement (indicated by reference numeral 28 in the same figure, BF-6M, produced by Oji Scientific Instruments) were hydrogen peroxide electrodes made of platinum having an immobilized enzyme membrane (thickness: 0.6 mm) on the surface. The immobilized enzyme membrane was obtained by immobilizing glucose oxidase (GOD) into a membrane. Electrolysis of hydrogen peroxide generated by the reaction of GOD in the immobilized membrane with glucose contained in the measurement sample was used to measure glucose.

A measurement sample was introduced into a sample supply opening 29 shown in FIG. 3c, and glucose was measured using the above-mentioned principle. Thereafter, stable HbA1c was measured by electrophoresis under the same electrophoresis conditions as those in Example 1. Table 12 shows the results.

TABLE 12

| | Within-run reproducibility test, CV (%) | |
|---|---|---|
| | Stable HbA1c | Glucose |
| Example 29 | 1.06 | 0.46 |
| Example 30 | 0.99 | 0.42 |

The CV value of the stable HbA1c values and the CV value of the glucose values obtained by the 10-time continuous measurement of the healthy human blood sample were as good as 1.06% and 0.46%, respectively. The measurement under the electrophoresis conditions of Example 2 using the material of the microchip used in Example 2 also favorably resulted in similar CV values. Microchips designed to have the same structure as that shown in FIG. 3a or 3b also achieved equivalent performance.

Example 31

A migration path coated with a cationic polymer immobilized thereon was used, and a buffer solution containing a water-soluble polymer having an anionic group was used as the electrophoresis buffer solution in Examples 31 and 32. Following separation of abnormal hemoglobins, the method for calculating stable HbA1c of the present invention was applied to examine its performance.

A migration path was formed on a microchip made of glass (50 mm×30 mm×2 mm), and a buffer solution reservoir was set for each end of the migration path.

A polyvinyl alcohol aqueous solution and 5% by weight aqueous solution of polybrene (produced by Wako Pure Chemical Industries, Ltd.) were sequentially allowed to flow through the migration path by the same method as in Example 1 for immobilization. The same electrophoresis buffer solution as that used in Example 1 was used.

The A2 control level 2 (produced by Bio-Rad Laboratories, Inc.) and the healthy human blood were mixed to prepare an evaluation sample containing HbA2, and the sample was adjusted to have a stable HbA1c value of 4.8%. The adjusted evaluation sample was added to the buffer solution reservoir set for one end of the migration path, and subjected to microchip electrophoresis by applying a voltage of 1000 V to both ends of the migration path. Transition of absorbance at 415 nm was measured to separate stable HbA1c from HbA2 in the evaluation sample.

FIG. 13 is the obtained electropherogram. In FIG. 13, the peak 1 represents HbA1a, the peak 2 represents HbA1b, the peak 3 represents HbF, the peak 4 represents unstable HbA1c, the peak 5 represents stable HbA1c, the peak 6 represents HbAo, and the peak 9 represents HbA2.

Peak area values of the respective Hbs of the obtained electropherogram were calculated. Each of the peak area values of the respective Hbs was divided by a peak area value (area value b) obtained by subtraction of an all-abnormal-Hb peak area value and the HbF peak area value from an all-Hb peak area value, and a percentage (%) of each Hb was calculated (the first measurement method).

The stable HbA1c peak area value (a) was divided by the sum of the area value (a) and the area value of HbAo (area value c), and a percentage (%) of each Hb was calculated (the second measurement method).

Table 13 shows the results.

Comparative Example 14

A percentage (%) of each Hb was calculated by following the same procedure as in Example 31, except that the peak area value of each Hb was divided by the all-Hb peak area value (area value d). Table 13 shows the results.

TABLE 13

| | | A1c (%) | | |
| --- | --- | --- | --- | --- |
| | | Example 32 | | |
| Peak No. | Component | Area value | First method | Second method | Comparative Example 14 |
| 1 | HbA1a | 183 | 1.1 | | 0.7 |
| 2 | HbA1b | 120 | 0.7 | | 0.5 |
| 3 | HbF | 5401 | | | 21.2 |
| 4 | Unstable HbA1c | 157 | 1.0 | | 0.6 |
| 5 | Stable HbA1c (Area value a) | 754 | 4.7 | 4.8 | 3.0 |
| 6 | HbAo | 14866 | 92.5 | 95.2 | 58.2 |
| 9 | HbA2 | 4052 | | | 15.9 |
| | Area value b | 16080 | | | |
| | Area value c | 15620 | | | |
| | Area value d | 25533 | | | |
| | | | 100.0 | 100.0 | 100.0 |

As shown in Table 13, the stable HbA1c values calculated by the first and second calculation methods in Example 31 were as accurate as about 4.8%. On the contrary, the value obtained by the calculation method in Comparative Example 14 was as inaccurate as 3.0%.

Example 32

A 0.2N hydrochloric acid aqueous solution containing 0.2% by weight of chitosan (produced by Wako Pure Chemical Industries, Ltd., chitosan 100) was prepared. Next, 0.2N—NaOH, ion exchange water, and 0.5N—HCl were allowed to flow through a capillary made of fused silica (produced by GL Sciences, Inc.: 25 μm in inside diameter×30 cm in full length) in this order to wash the inside of the capillary, and then the prepared chitosan aqueous solution was allowed to flow through the capillary for 20 minutes. Subsequently, air was injected into the capillary to send out the chitosan aqueous solution, and then the capillary was dried in a drier at a temperature of 40° C. for 12 hours. Thereafter, the chitosan aqueous solution was injected again, and the procedure of injection of air and drying was repeated 5 times.

The chitosan immobilized capillary was set in a capillary electrophoresis apparatus (produced by Beckman Coulter, Inc., PAC/E MDQ). Subsequently, a citrate buffer solution (pH 4.8) containing 2.0% by weight of chondroitin sulfate (produced by Wako Pure Chemical Industries, Ltd.) was used as the electrophoresis buffer solution, and set for both ends of the capillary to fill the capillary with the buffer solution.

The AFSC hemocontrol (produced by Helena Laboratories) and the healthy human blood were mixed to prepare an evaluation sample containing abnormal Hbs with a stable HbA1c value of 5.0%. The prepared evaluation sample was injected into the capillary from one end, and subjected to electrophoresis by applying a voltage of 20 kV to the buffer solutions set for the ends of the capillary. Transition of visible light absorbance at 415 nm was measured to check separation of stable HbA1c and the abnormal Hbs.

FIG. 14 is the obtained electropherogram. In FIG. 14, the peak 1 represents HbA1a, and peak 2 represents HbA1b, the peak 3 represents fetal Hb (HbF), the peak 4 represents unstable HbA1c, the peak 5 represents stable HbA1c, the peak 6 represents HbAo, the peak 7 represents HbS, and the peak 8 represents HbC.

Peak area values of the respective Hbs of the obtained electropherogram were calculated. Each of the peak area values of the respective Hbs was divided by a peak area value b obtained by subtraction of an all-abnormal-Hb peak area value and the HbF peak area value from an all-Hb peak area value, and a percentage (%) of each Hb was calculated (the first calculation method).

The stable HbA1c peak area value a was divided by the sum of the peak area value a and the HbAo peak area value c, and a percentage (%) of each Hb was calculated (the second measurement method).

Table 14 shows the results.

Comparative Example 15

A percentage (%) of each Hb was calculated by following the same procedure as in Example 32, except that the peak area value of each Hb was divided by the all-Hb peak area value.

TABLE 14

| | | A1c (%) | | |
| --- | --- | --- | --- | --- |
| | | Example 32 | | |
| Peak No. | Component | Area value | First method | Second method | Comparative Example 15 |
| 1 | HbA1a | 143 | 1.1 | | 0.4 |
| 2 | HbA1b | 100 | 0.8 | | 0.3 |
| 3 | HbF | 7039 | | | 19.0 |
| 4 | Unstable HbA1c | 156 | 1.2 | | 0.4 |
| 5 | Stable HbA1c (Area value a) | 641 | 4.9 | 5.1 | 1.7 |

TABLE 14-continued

| | | | Alc (%) | | |
| | | | Example 32 | | |
| Peak No. | Component | Area value | First method | Second method | Comparative Example 15 |
|---|---|---|---|---|---|
| 6 | HbAo | 11987 | 92.0 | 94.9 | 32.4 |
| 7 | HbS | 8998 | | | 24.3 |
| 8 | HbC | 7892 | | | 21.4 |
| | Area value b | 13027 | | | |
| | Area value c | 12628 | | | |
| | Area value d | 36956 | | | |
| | | | 100.0 | 100.0 | 100.0 |

As shown in Table 14, the stable HbA1c values calculated by the first calculation method and the second calculation method in Example 32 were as accurate as about 5.0%. On the contrary, the stable HbA1c value calculated by the calculation method in Comparative Example 15 was as inaccurate as 1.7%.

INDUSTRIAL APPLICABILITY

The present invention can provide a method for measuring hemoglobin that enables short-time, high-accuracy measurement of hemoglobin, in particular stable hemoglobin A1c, which is used as a diagnostic indicator of diabetes mellitus, and an electrophoresis apparatus that is suitably used in this measurement method.

EXPLANATION OF SYMBOLS

Figure 1:
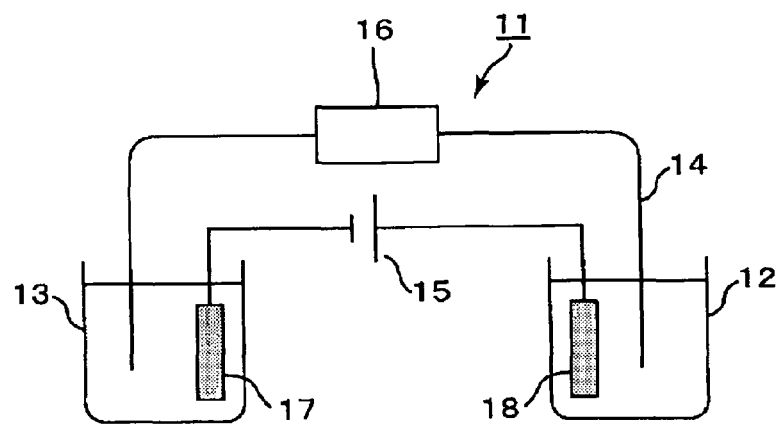
FIG. 1 is a schematic view showing an example of a capillary electrophoresis apparatus used in a method for measuring hemoglobin of the present invention.
Figure 2A:
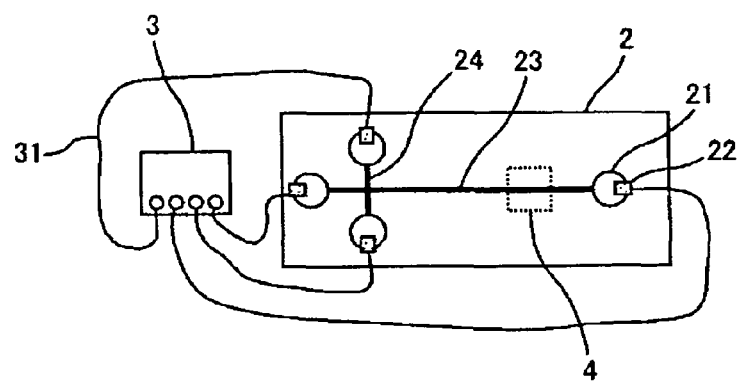
FIG. 2a is a top view schematically showing a microdevice electrophoresis apparatus of the present invention.
Figure 2B:
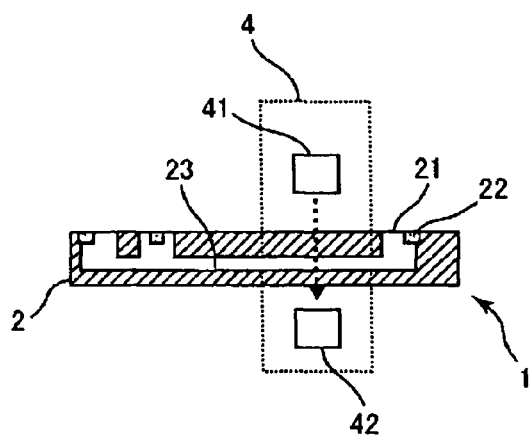
FIG. 2b is a transverse cross-sectional view schematically showing the microdevice electrophoresis apparatus of the present invention.
Figure 3A:
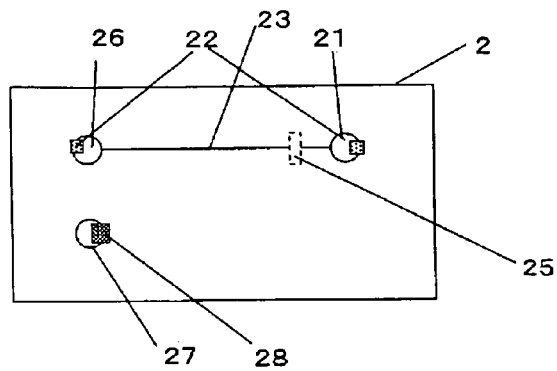
FIG. 3a is a schematic view showing an example of the microdevice electrophoresis apparatus of the present invention provided with a glucose measurement mechanism.
Figure 3B:
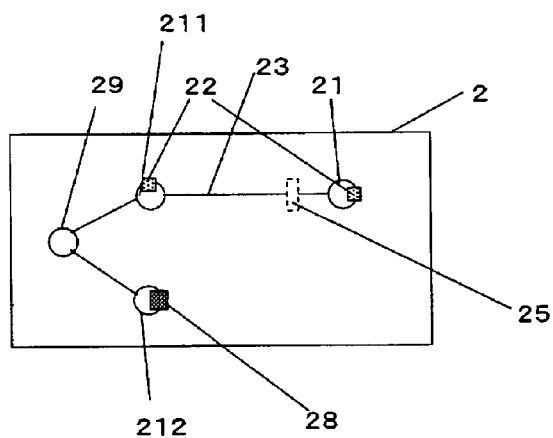
FIG. 3b is a schematic view showing another example of the microdevice electrophoresis apparatus of the present invention provided with a glucose measurement mechanism.
Figure 3C:
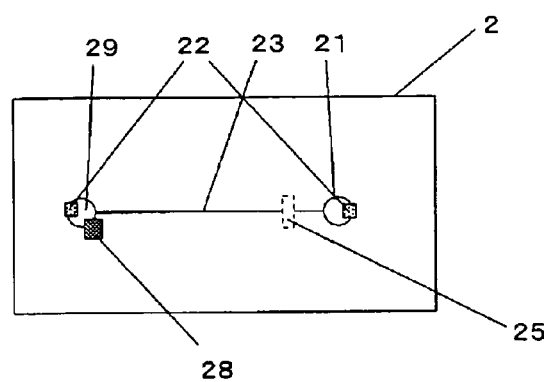
FIG. 3c is a schematic view showing still another example of the microdevice electrophoresis apparatus of the present invention provided with a glucose measurement mechanism.
Figure 4:
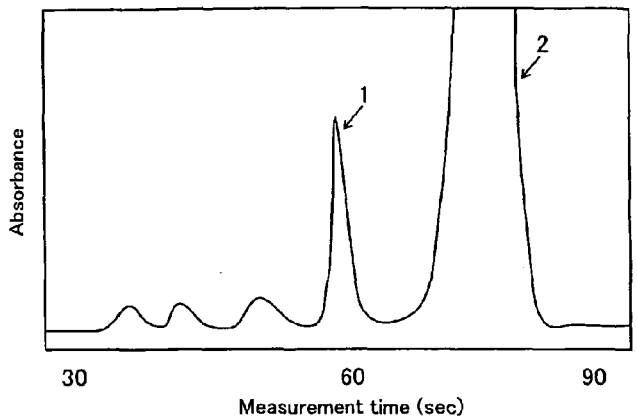
FIG. 4 is an electropherogram obtained by measurement of a healthy human blood sample in Example 1.
Figure 5:
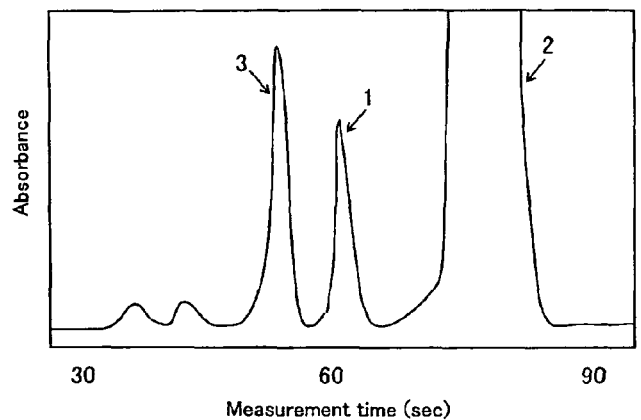
FIG. 5 is an electropherogram obtained by measurement of a sample containing a modified Hb in Example 1.
Figure 6:
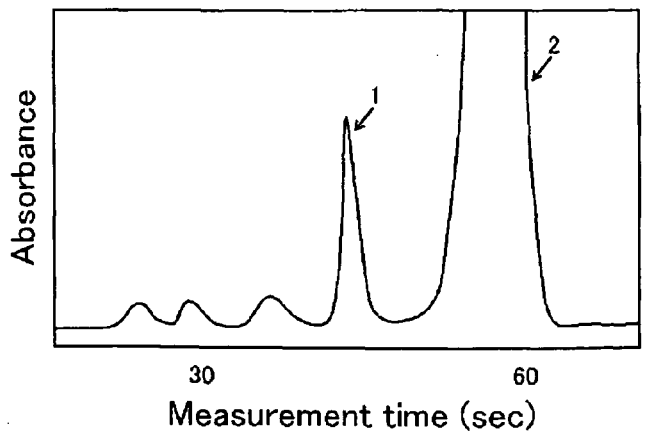
FIG. 6 is an electropherogram obtained in Example 3 by measurement of the healthy human blood sample prepared in the process (3) of Example 1.
Figure 7:
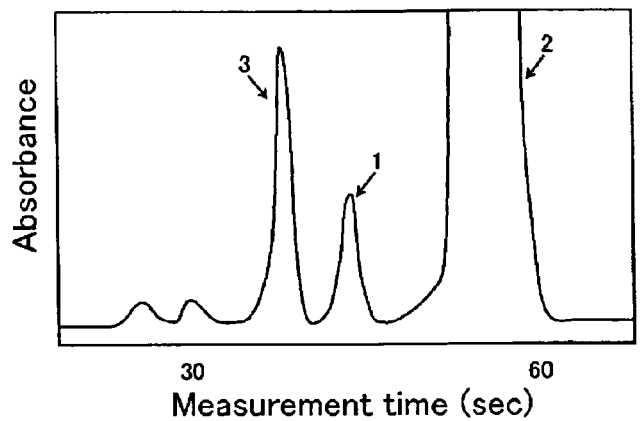
FIG. 7 is an electropherogram obtained in Example 3 by measurement of the sample containing the modified Hb prepared in the process (4) of Example 1.
Figure 8:
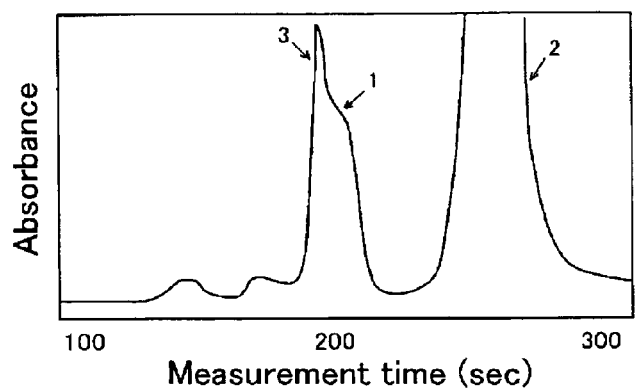
FIG. 8 is an electropherogram obtained by measurement of a sample containing the modified Hb in Comparative Example 2.
Figure 9:
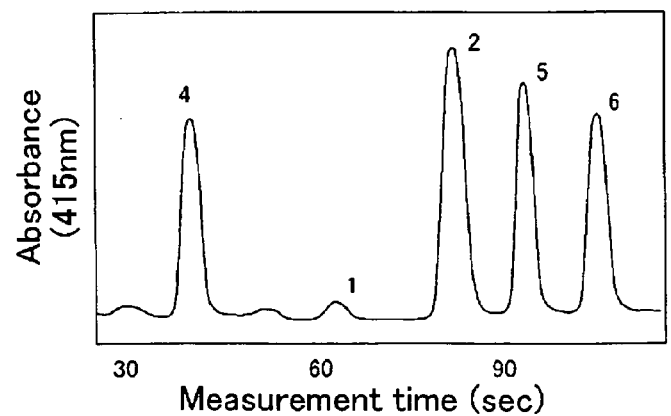
FIG. 9 is an electropherogram obtained by measurement of a sample containing HbS and HbC as abnormal Hbs in Example 24 by electrophoresis performed by following the same procedure as in the measurement of the healthy human sample.
Figure 10:
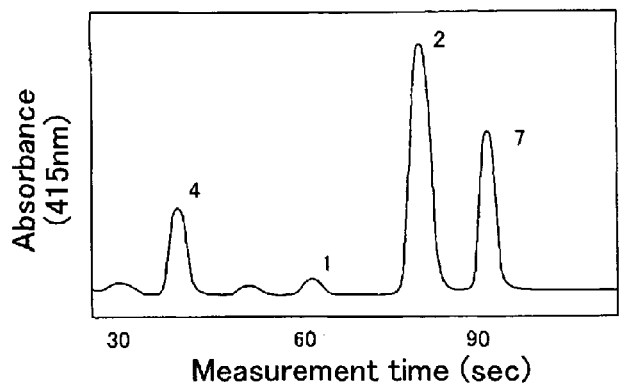
FIG. 10 is an electrophoresis obtained by measurement of a sample containing HbA2 in Example 24 by electrophoresis performed by following the same procedure as in the measurement of the healthy human sample.
Figure 11:
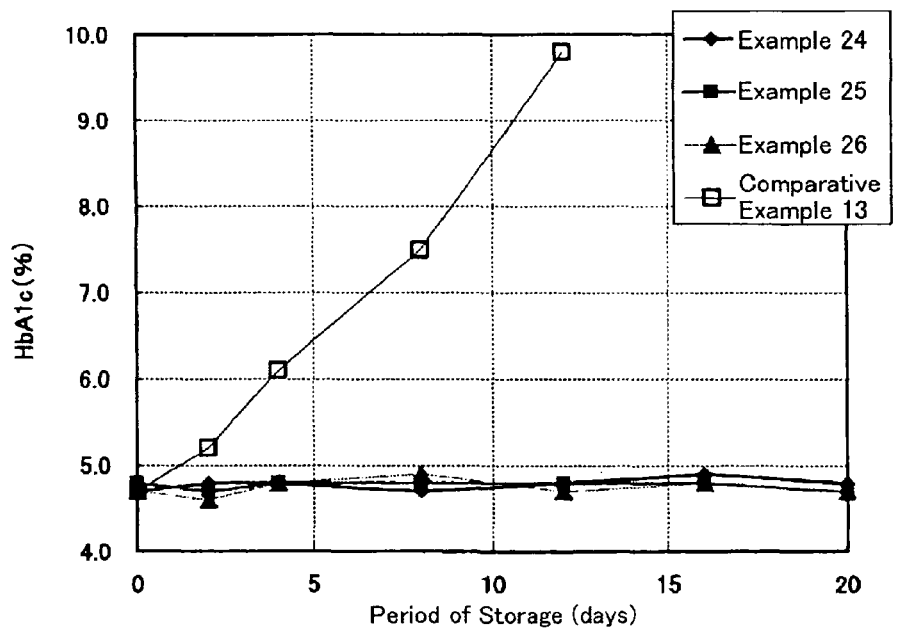
FIG. 11 is a graph showing the relationship of stable HbA1c values (%) obtained by measurement by electrophoresis and storage days in Examples 24 to 26 and Comparative Example 12.
Figure 12A:
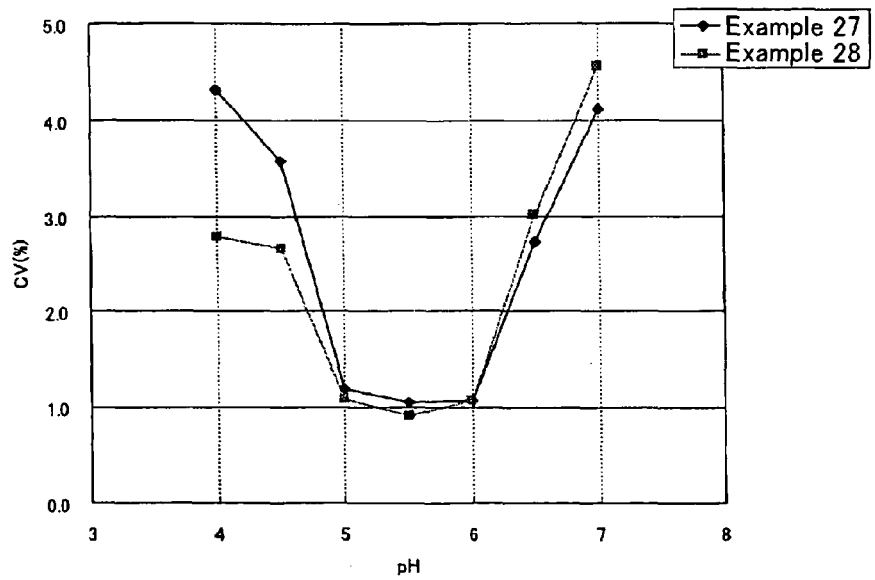
FIG. 12a is a graph showing results of the within-run reproducibility test in Examples 27 and 28 in which the pHs of citrate buffer solutions were changed.
Figure 12B:
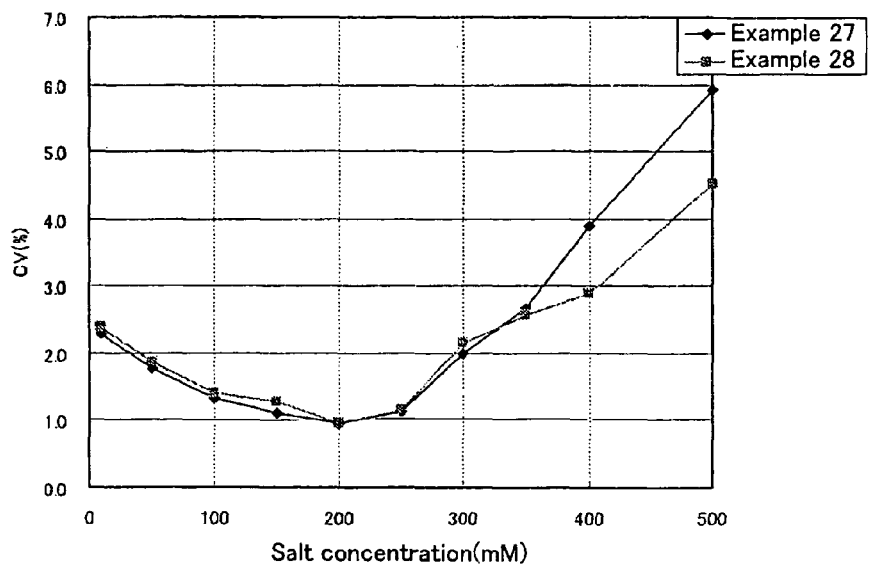
FIG. 12b is a graph showing results of the within-run reproducibility test in Examples 27 and 28 in which the salt concentrations of the citrate buffer solutions were changed.
Figure 13:
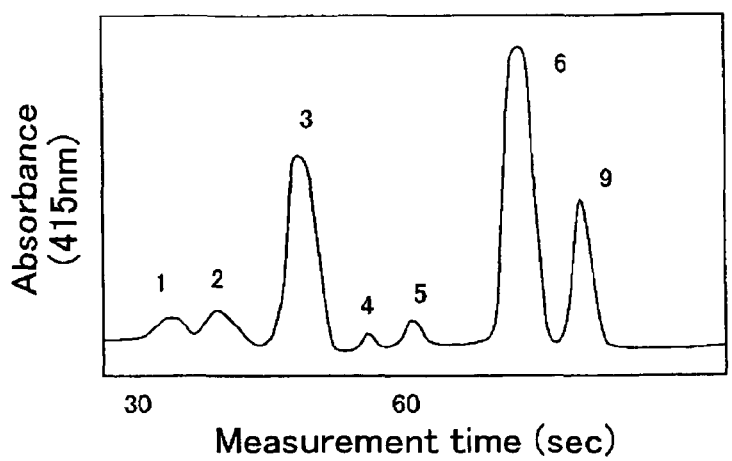
FIG. 13 is an electropherogram obtained in Example 31.
Figure 14:
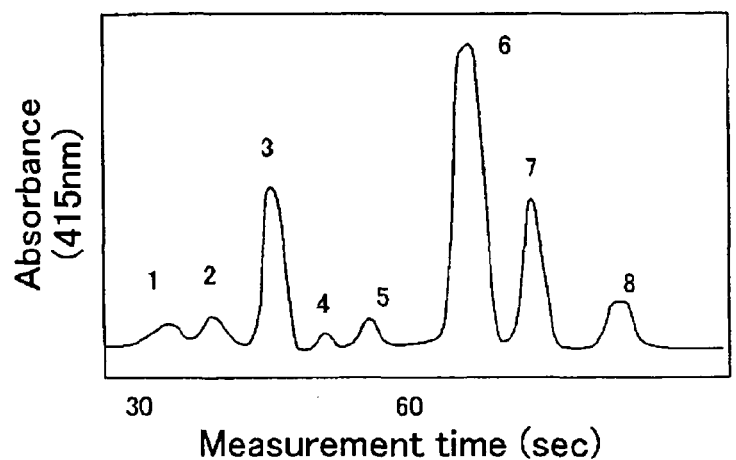
FIG. 14 is an electropherogram obtained in Example 32.

11 Capillary electrophoresis apparatus
12 Anode reservoir
13 Cathode reservoir
14 Capillary
15 High-voltage power supply
16 Detector
17,18 Electrode
2 Measurement unit
21 Reservoir
211 Reservoir for hemoglobin measurement
212 Reservoir for glucose measurement
22 Electrode
23 Migration path
25 Detection position
26 Sample supply opening for hemoglobin measurement
27 Sample supply opening for glucose measurement
28 Enzymatic electrode
29 Sample supply opening (for both)
3 Power supply unit
31 Voltage supply cable 31
4 Detection unit
41 Light source
42 Light receiving part

The invention claimed is:

1. A method for measuring hemoglobin using electrophoresis,
which comprises:
providing a migration path having an inner surface coated with a cationic substance, wherein the cationic substance is immobilized on the inner surface by heating or drying after contacting the cationic substance to the inner surface of the migration path or by covalently binding the cationic substance to the inner surface of the migration path, wherein the cationic substance is a cationic polymer, wherein the cationic polymer is immobilized on a coating layer of an immobilized non-ionic hydrophilic polymer, wherein the cationic polymer forms the innermost layer of the migration path;
applying an electrophoresis buffer solution containing a water-soluble polymer having an anionic group as an electrophoresis buffer solution to the migration path,
applying a sample containing hemoglobin to the migration path,
performing electrophoresis on the sample, and
measuring hemoglobin in the sample.

2. The method for measuring hemoglobin according to claim 1, wherein the inner surface of the migration path is further ozonized.

3. The method for measuring hemoglobin according to claim 1, wherein the migration path is filled with an ion exchanger.

4. The method for measuring hemoglobin according to claim 1, wherein the water-soluble polymer having an anionic group contained in the electrophoresis buffer solution is a sulfated polysaccharide.

5. The method for measuring hemoglobin according to claim 1, wherein the water-soluble polymer having an anionic group is a water-soluble acrylic polymer having an anionic group.

6. The method for measuring hemoglobin according to claim 5, wherein the anionic group of the water-soluble polymer having an anionic group is a sulfonic acid group.

7. The method for measuring hemoglobin according to claim 1, wherein the electrophoresis buffer solution further contains a chaotropic compound.

8. The method for measuring hemoglobin according to claim 1, wherein the electrophoresis buffer solution further contains a nitrite.

9. A method for simultaneously measuring stable hemoglobin A1c and abnormal hemoglobins, which comprises using the method for measuring hemoglobin according to claim 1.

10. A method for calculating a stable hemoglobin A1c value using the method for measuring hemoglobin according to claim 1,
which comprises, in an electropherogram having a stable hemoglobin A1c peak, abnormal hemoglobin peaks and a fetal hemoglobin peak each separated from each other, calculating a stable hemoglobin A1c value by the formula (1) given below using a stable hemoglobin A1c peak area value a and a peak area value b obtained by subtraction of peak area values of abnormal hemoglobins and a peak area value of fetal hemoglobin from a peak area value of all hemoglobins

[Formula 1]

$$\text{Stable Hemoglobin } A1c \text{ value} = \frac{\text{Peak Area Value } a}{\text{Peak Area Value } b} \times 100(\%). \quad (1)$$

11. A method for calculating a stable hemoglobin A1c value using the method for measuring hemoglobin according to claim 1,
which comprises, in an electropherogram having a stable hemoglobin A1c peak and a hemoglobin Ao peak each separated from one another, calculating a stable hemoglobin A1c value by the formula (2) given below using a stable hemoglobin A1c peak area value a and a hemoglobin Ao peak area value c

[Formula 2]

$$\text{Stable Hemoglobin } A1c \text{ value} = \frac{\text{Peak Area Value } a}{\text{Peak Area Value } a + \text{Peak Area Value } c} \times 100(\%). \quad (2)$$

\* \* \* \* \*